US 6,589,169 B1

(12) United States Patent
Surwit et al.

(10) Patent No.: US 6,589,169 B1
(45) Date of Patent: Jul. 8, 2003

(54) SYSTEMS, METHODS AND COMPUTER PROGRAM PRODUCTS FOR MONITORING, DIAGNOSING AND TREATING MEDICAL CONDITIONS OF REMOTELY LOCATED PATIENTS UNDERGOING ANTICOAGULATION THERAPY

(75) Inventors: Richard S. Surwit, Chapel Hill, NC (US); Lyle M. Allen, III, Durham, NC (US); Sandra E. Cummings, Chapel Hill, NC (US)

(73) Assignee: Healthware Corporation, Chapel Hill, NC (US)

( * ) Notice: Subject to any disclaimer, the term of this patent is extended or adjusted under 35 U.S.C. 154(b) by 0 days.

(21) Appl. No.: 09/470,774

(22) Filed: Dec. 23, 1999

Related U.S. Application Data

(63) Continuation of application No. 09/042,048, filed on Mar. 13, 1998, now Pat. No. 6,024,699.

(51) Int. Cl.[7] ................................................. A61B 5/00
(52) U.S. Cl. ....................... 600/300; 128/903; 128/904; 128/920; 128/921
(58) Field of Search ................................. 600/300, 301, 600/365; 128/903, 904, 920, 921

(56) References Cited

U.S. PATENT DOCUMENTS

| | | |
|---|---|---|
| 4,685,059 A | 8/1987 | Yamamoto |
| 4,731,726 A | 3/1988 | Allen, III |
| 4,803,625 A | 2/1989 | Fu et al. |
| 4,981,139 A | 1/1991 | Pfohl |
| 5,016,172 A | 5/1991 | Dessertine |
| 5,019,974 A | 5/1991 | Beckers |

(List continued on next page.)

FOREIGN PATENT DOCUMENTS

| | | |
|---|---|---|
| EP | 0 251 520 A2 | 1/1988 |
| EP | 0 555 590 A2 | 8/1993 |
| WO | WO 96/27163 | 9/1996 |
| WO | WO 99/04043 | 1/1999 |

OTHER PUBLICATIONS

J.D. Piette; *Moving Diabetes management From Clinic to Community: Development of a Prototype Based on Automated Voice messaging: The Diabetes Educator* 23,No. 6:672–680 (1997).

(List continued on next page.)

Primary Examiner—Eric F. Winakur
(74) Attorney, Agent, or Firm—Myers Bigel Sibley & Sajovec

(57) ABSTRACT

Medical conditions of a plurality of remotely located patients are monitored, diagnosed, prioritized and treated using a central data processing system configured to communicate with and receive data from a plurality of respective patient monitoring systems. Patient monitoring systems are capable of receiving and storing patient data and may include a medicine dosage algorithm for using the stored patient data to generate medicine dosage recommendations to a patient. A central data processing system is configured to obtain patient data from each patient monitoring system and analyze the obtained patient data to identify medical conditions of each respective patient. A central data processing system may include medicine dosage algorithms. Identified patient medical conditions for each respective patient are displayed in selectable, prioritized order according to medical severity via one or more remotely located clients in communication with a central data processing system. Modifications to medicine dosages, medicine dosage algorithms, patient fixed or contingent self-monitoring schedules, as well as other treatment information, may be communicated directly to a patient or to a patient monitoring system.

59 Claims, 16 Drawing Sheets

U.S. PATENT DOCUMENTS

| | | |
|---|---|---|
| 5,024,225 A | 6/1991 | Fang |
| 5,025,374 A | 6/1991 | Roizen et al. |
| 5,047,044 A | 9/1991 | Smith et al. ................ 606/182 |
| 5,077,476 A | 12/1991 | Rosenthal |
| 5,078,134 A | 1/1992 | Heilman et al. |
| 5,216,597 A | 6/1993 | Beckers |
| 5,265,613 A | 11/1993 | Feldman et al. |
| 5,307,263 A | 4/1994 | Brown |
| 5,341,291 A | 8/1994 | Roizen et al. |
| 5,371,687 A | 12/1994 | Holmes, II et al. |
| 5,379,214 A | 1/1995 | Arbuckle et al. |
| 5,432,698 A | 7/1995 | Fujita |
| 5,458,123 A | 10/1995 | Unger |
| 5,471,382 A | 11/1995 | Tallman et al. |
| 5,579,775 A | 12/1996 | Dempsey et al. |
| 5,619,991 A | 4/1997 | Sloane ....................... 600/300 |
| 5,822,715 A | 10/1998 | Worthington et al. ......... 702/19 |
| 5,840,020 A | 11/1998 | Hainonen et al. ........... 128/904 |
| 5,907,291 A | 5/1999 | Chen et al. ................. 600/300 |

OTHER PUBLICATIONS

J.E. Ansell et al; *Long–term Patient Self–management of Oral Anticoagulation*, Arch Intern Med 155:2185–2189 (1995).

Puers, B. et al., "Patient Monitoring Systems," VLSI and Computer Peripherals, Hamburg, Conf. No. 3, pp. 3–152–157 (May 8, 1989).

Benaroch, Lee M. et al., "A New Approach to Computer Directed Insulin Management Systems: DiaComp," Proceedings of the Annual Symposium on Computer Based Medical Systems, Minneapolis, Symp. 2, pp. 89–96 (Jun. 26, 1989).

FIG. 10A.

| Assesments | Breakfast | Lunch | Dinner | Late Night |
|---|---|---|---|---|
| | 18u Lente @Dinner Avg. BG 120 | 5u Semi-Lente @Breakfast Avg. BG 100 | 12u Lente @Breakfast Avg. BG 130 | 6u Semi-Lente @Dinner Avg. BG 115 |
| Adjustment | Enabled | Enabled | Enabled | Enabled |
| Increase if BG above | 100 | 130 | 140 | 140 |
| for Consec Days | 3 | 3 | 3 | 3 |
| Decrease if BG below | 50 | 55 | 55 | 55 |
| for Consec Days | 4 | 2 | 2 | 2 |
| Method | Percent ▷ | Units ▷ | Percent ▷ | Units ▷ |
| Amount | 10% | 1 | 5% | 1 |

SYSTEMS, METHODS AND COMPUTER PROGRAM PRODUCTS FOR MONITORING, DIAGNOSING AND TREATING MEDICAL CONDITIONS OF REMOTELY LOCATED PATIENTS UNDERGOING ANTICOAGULATION THERAPY

RELATED APPLICATIONS

This application is a continuation of U.S. patent application Ser. No. 09/042,048, filed on Mar. 13, 1998, now U.S. Pat. No. 6,024,699.

FIELD OF THE INVENTION

The present invention relates generally to data processing systems, methods and computer program products and, more particularly, to medical data processing systems, methods and computer program products.

BACKGROUND OF THE INVENTION

Chronic disease management conventionally involves routinely monitoring patients to identify health problems before they become medically severe. Chronic disease management may also involve monitoring exercise and diet patterns of patients, as well as adherence to and adjustments of prescribed medicine. A chronic disease that is a major health problem in the United States, and one that often reduces the life span of those who suffer from it, is diabetes mellitus. Diabetes mellitus relates to a group of disorders in which the human body does not produce sufficient insulin and, as a result, blood sugar is elevated. Diabetes management conventionally includes monitoring a patient's blood glucose for abnormalities; monitoring preventative health behaviors such as weight control and fat intake; and monitoring adherence to scheduled insulin regimens.

An important advance in diabetes treatment has been the advent of home blood glucose monitoring wherein glucose meters are used by patients to self-test blood-glucose levels. However, control of blood glucose may require that patients measure their blood sugar 3–4 times per day, record the data, use the data in a formula to adjust their insulin dosage, and frequently communicate the data to a physician or nurse to evaluate their progress. Unfortunately, physicians may not have the time required to review blood glucose data from patients on a regular basis, or to educate and/or motivate patients to follow complicated self-care regimens. Furthermore, some physicians may consider data obtained by patients unreliable and may require patients to come in for an office visit for testing. Requiring patients to make office visits may increase the cost of health care, and may reduce the likelihood that frequent (i.e., daily) adjustments to insulin levels are made.

To overcome the disadvantages of requiring diabetes patients to visit a physician's office, various health care organizations have implemented programs where case managers (i.e., persons with some level of medical training) telephone patients periodically to obtain blood glucose data and other information and to coordinate care. Unfortunately, with often hundreds of patients per case manager, personal contact with individual patients on a daily or even regular basis may be difficult. In addition, personal contact with individual patients on a regular basis may be somewhat expensive. Accordingly, case managers using conventional management techniques may not be able to adjust a patient's insulin dosage as often as necessary to adequately control blood glucose level.

In addition, patients with diabetes may often need feedback and encouragement to continue testing their glucose levels and reporting results to a case manager. Without regular positive feedback, patients may not perform self-tests with enough regularity or may not conduct tests properly.

Another approach used in chronic disease management involves automated voice messaging (AVM) services, wherein patients receive regular telephone calls providing various educational and motivational messages from case managers. Exemplary messages may include reminding a patient of a scheduled physician visit. Some AVM services involve one-way communication, wherein a recorded message is delivered to a patient, but no information is obtained from the patient. As a result, the medical condition of a patient may not be available unless the patient is examined in-person by a physician.

AVM services involving two-way communications may allow patients to respond to AVM telephone queries via a touch tone telephone. Information received from patients may be reviewed by a case manager. The case manager then may identify which patients require callbacks for gathering more detailed information, discussing problems, or providing further information. Unfortunately, AVM services involving two-way communications may require some level of human intervention to identify patients with medically severe conditions that require medical attention, such as a change in insulin dosage. Chronic disease management via AVM has another drawback in that delays may occur between the identification of a patient with a medically severe condition and actual treatment of the condition.

SUMMARY OF THE INVENTION

In view of the above discussion, it is an object of the present invention to allow health care providers to quickly and easily monitor many patients simultaneously and to automatically identify patients with medical conditions and to organize identified medical conditions by severity.

It is yet another object of the present invention to allow health care providers to quickly prepare revised medicine dosages for patients and quickly communicate revised dosage information to patients.

It is also an object of the present invention to facilitate effective patient behavior modification in remotely located patients by providing timely rewards for correct behavior.

These and other objects of the present invention are provided by methods, systems and computer program products for monitoring, diagnosing, prioritizing and treating medical conditions of a plurality of remotely located patients undergoing anticoagulation therapy using a central data processing system configured to communicate with and receive data from a plurality of respective patient monitoring systems. Patient monitoring systems are capable of receiving and storing patient data and may include a medicine dosage algorithm for using the stored patient data to generate medicine dosage recommendations to a patient.

A central data processing system may be configured to obtain patient data from each patient monitoring system, to analyze the obtained patient data, and to identify medical conditions requiring medical attention. A central data processing system may also implement medication dosage algorithms in cases where these algorithms are not a feature offered by patient monitoring systems.

Data transmitted from a patient monitoring system may be analyzed substantially simultaneously with the transmission thereof to the central data processing system to identify emergency medical conditions requiring immediate medical attention. For identified emergency medical conditions, treatment information and altered self-monitoring instructions and/or prompts may be automatically communicated to the respective patient monitoring system.

Identified patient medical conditions for each respective patient are displayed in selectable, prioritized order according to medical severity via one or more remotely located client machines (hereinafter "clients") in communication with a central data processing system. In response to a user (e.g., a case manager, physician, nurse) selecting an identified medical condition for a respective patient, treatment options for treating the medical condition may be displayed on the client.

A user may communicate treatment information to a respective patient via a variety of methods including, but not limited to, wireless, satellite, telephone, AVM, e-mail, or facsimile transmission. In addition, the present invention allows a user to communicate treatment information directly from a client to a respective patient monitoring system or within a central data processing system. A user may modify a medicine dosage algorithm stored within a respective patient monitoring system or within a central data processing system. In addition to modifying dosage algorithms, a user may modify medicine doses and fixed or contingent self-monitoring schedules for a patient. The present invention also tracks each identified medical condition for each patient from identification to resolution. The present invention tracks whether a user has communicated treatment information to a patient regarding an identified medical condition. In addition, the present invention tracks whether a patient has performed actions associated with treatment recommended by a user.

According to another aspect of the present invention, patient monitoring devices for monitoring medical conditions of a patient are configured to receive, store and analyze patient-obtained data. For example, a patient may take a blood sample and have the sample analyzed and stored within a device. Patient monitoring devices are configured to communicate with and transmit stored patient data to a central data processing system. Patient monitoring devices are also configured to receive treatment information from the central data processing system. For example, information may be displayed to a patient via a patient monitoring device. In addition, a medicine dosage algorithm may be stored within a patient monitoring device and may be modified via a central data processing system to adjust a patient's medicine dosage.

According to another aspect of the present invention, a system for monitoring medical conditions of a plurality of remotely located patients includes a central data processing system configured to communicate with a plurality of remotely located patient monitoring systems and at least one remotely located client in communication with the central data processing system. A central data processing system is configured to obtain patient data from each remotely located patient monitoring system and to analyze the obtained patient data to identify medical conditions of each respective patient. Identified patient medical conditions for each respective patient may be displayed to a user in selectable, prioritized order according to medical severity via a remotely located client. By selecting a particular medical condition for a patient, treatment options for treating the selected medical condition may be displayed to the user.

A central data processing system, according to the present invention, is configured to allow a user to communicate treatment information to a respective patient via a client in various methods through the central data processing system, including, but not limited to, wireless, satellite, telephone, AVM, e-mail, or facsimile transmission. A user may also transmit motivational and other behavior-modification information to a patient via a client through the central data processing system. In addition, a central data processing system is configured to allow a user to transmit treatment information directly to a patient's remotely located patient monitoring system via a client. For example, modifications may be made directly to a medicine dosage algorithm stored within a respective patient monitoring system.

A central data processing system, according to the present invention, may also be configured to analyze data transmitted from a patient monitoring system substantially simultaneously with the transmission thereof to identify emergency medical conditions requiring immediate medical attention or to calculate a new medication dosage according to a physician-prescribed algorithm. In response to identifying an emergency medical condition, treatment information may be automatically communicated to the respective patient monitoring system while communications are still established.

The present invention is advantageous because physicians and other health care providers can remotely monitor, identify and treat patient medical problems, thereby obviating the need for frequent patient visits and telephone calls. The present invention facilitates automation of various aspects of patient treatment. In addition, physicians and case managers utilizing the present invention are able to quickly identify patients with medical conditions requiring immediate attention from a patient population of thousands or more. For example, the present invention can regulate warfarin dosage without requiring patients to be seen by a physician. A patient's progress can be continuously monitored and changes can be made to a patient's warfarin dosage, to a patient's dosage algorithm, and to a patient's fixed or contingent self-monitoring scheduling as often as necessary.

Using the present invention, anticoagulation therapy patients can transmit data to a central data processing system at specified intervals and the data can be analyzed to detect trends and problems. If a problem with a particular patient is detected, a revised warfarin (or other anticoagulation medicine) algorithm, a revised warfarin (or other anticoagulation medicine) dosage, and a revised fixed or contingent self-monitoring schedule can be downloaded to that patient's monitoring system, or can be transmitted directly to the patient. In addition the patient can be notified either by telephone, AVM, e-mail or fax to seek immediate medical attention if necessary.

The present invention is particularly well-suited for facilitating patient behavior modification. Through prompts and useful feedback, the present invention can reward patients for proper self care behavior.

BRIEF DESCRIPTION OF THE DRAWINGS

FIGS. 10A–10C illustrate exemplary user interfaces for facilitating communications with a remotely located patient.

FIG. 11 illustrates an exemplary user interface for adjusting a medicine dosage algorithm stored within a patient's PPM.

FIG. 12 illustrates an exemplary user interface for seeking input from other medical experts.

FIG. 14 illustrates an exemplary user interface for removing an identified medical condition from an active list.

DETAILED DESCRIPTION OF THE INVENTION

Figure 1:
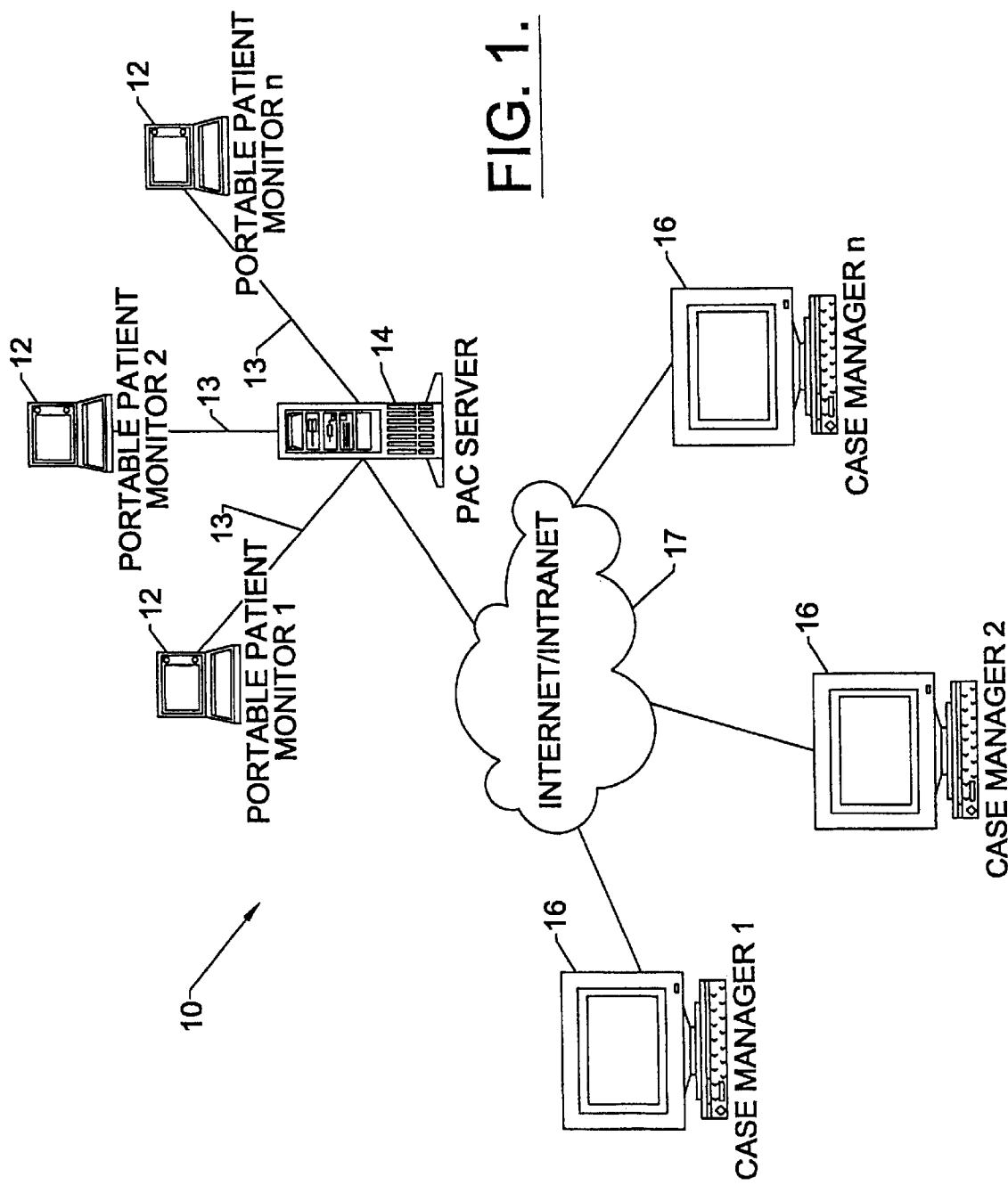
FIG. 1 schematically illustrates a system for monitoring, diagnosing and treating medical conditions of a plurality of remotely located patients according to an embodiment of the present invention.

The present invention now is described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. The present invention will now be described more fully hereinafter with reference to the accompanying drawings, in which preferred embodiments of the invention are shown. Like numbers refer to like elements throughout.

As will be appreciated by one of skill in the art, the present invention may be embodied as a method, data processing system, or computer program product. Accordingly, the present invention may take the form of an entirely hardware embodiment, an entirely software embodiment or an embodiment combining software and hardware aspects. Furthermore, the present invention may take the form of a computer program product on a computer-readable storage medium having computer-readable program code means embodied in the medium. Any suitable computer readable medium may be utilized including hard disks, CD-ROMs, optical storage devices, or magnetic storage devices.

The present invention is described below with reference to flowchart illustrations of methods, apparatus (systems) and computer program products according to embodiments of the invention. It will be understood that each block of the flowchart illustrations, and combinations of blocks in the flowchart illustrations, can be implemented by computer program instructions. These computer program instructions may be loaded onto a general purpose computer, special purpose computer, or other programmable data processing apparatus to produce a machine, such that the instructions which execute on the computer or other programmable data processing apparatus create means for implementing the functions specified in the flowchart block or blocks.

These computer program instructions may also be stored in a computer-usable memory that can direct a computer or other programmable data processing apparatus to function in a particular manner, such that the instructions stored in the computer-usable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Accordingly, blocks of the flowchart illustrations support combinations of means for performing the specified functions, combinations of steps for performing the specified functions and program instruction means for performing the specified functions. It will also be understood that each block of the flowchart illustrations, and combinations of blocks in the flowchart illustrations, can be implemented by special purpose hardware-based computer systems which perform the specified functions or steps, or combinations of special purpose hardware and computer instructions.

Computer program for implementing the present invention may be written in various object-oriented programming languages, such as Delphi and Java®. However, it is understood that other object oriented programming languages, such as C++ and Smalltalk, as well as conventional programming languages, such as FORTRAN or COBOL, could be utilized without departing from the spirit and intent of the present invention.

System Overview

Referring now to FIG. 1, a system 10 for monitoring, diagnosing, and treating medical conditions of remotely located patients with various chronic illnesses, according to the present invention, is schematically illustrated. A plurality of portable patient monitors (PPMs) 12 are configured to establish communications directly with a central data processing system referred to as a Physicians Access Center server (hereinafter "PAC server") 14 via communications links 13. A plurality of case manager clients (CMCs) 16 are configured to establish client-server communications with the PAC server 14 via a computer network 17, such as the Internet or an Intranet. It is understood that a CMC or PAC server or other apparatus configured to execute program code embodied within computer usable media, operates as means for performing the various functions and carries out the methods of the various operations of the present invention. It is also understood that the present invention may be used with various client-server communications protocols, and is not limited to specific protocols such as TCP/IP protocol.

Each of these components will be described in detail below. The present invention will be described throughout this disclosure with respect to the control of blood glucose for diabetes patients. However, it is to be understood that the present invention may be utilized with a wide variety of medical conditions including, but not limited to, anticoagulant therapy for stroke prevention, asthma, diabetes, and other chronic diseases. For example a PPM may collect and use patient data to adjust medication dosage for respiratory therapy and anticoagulation therapy based on predefined physician prescriptions. As is well known to those of skill in the art of anticoagulation therapy, prothrombin (PT) tests are commonly used in monitoring the efficacy of anticoagulation therapy. Also, as is well known to those of skill in the art of anticoagulation therapy, warfarin is a commonly used anticoagulation medication.

The term "prescription" may include physician-prescribed algorithms for calculating medicine dosages, dosages calculated from algorithms, and fixed and contingent self-monitoring schedules for patients. An exemplary physician-prescribed medication algorithm is described in *Guidelines for the Diagnosis and Management of Asthma; Expert Panel Report Two*; National Institutes of Health; Heart and Lung Institute; Publication No.: 97-4051, April 1997, which is incorporated herein by reference in its entirety. Another exemplary physician-prescribed medication algorithm is described in *Long-term Patient Self-management of Oral Anticoagulation*; Jack E. Ansell et al.; Arch Intern Med. 1995; Vol. 155; pp. 2185–2189; which is incorporated herein by reference in its entirety.

A PPM may incorporate physician-prescribed algorithms for calculating medicine dosages for various chronic illnesses. Alternatively, a PAC server may implement a medication dosage algorithm for anticoagulation therapy, based on values communicated to the PAC server by a PPM, and communicate results directly to the patient. PAC server implemented dosage algorithms may be a logical alternative to having medication dosage algorithms stored within PPMs when medication dosage changes are infrequent.

Portable Patient Monitors (PPM)

A PPM (12 in FIG. 1) serves as primary means for collecting data from a patient and as means for case managers to interface with a patient. Exemplary features of a PPM for use in accordance with the present invention are summarized below in Table 1.

TABLE 1

Small and portable so patient can carry around.
Data processing capabilities and built-in
modem or attachable external modem.
Collects data from blood, breath or bodily
fluids or other functions.
Collects patient supplied data on health
status, compliance to medical regime, and
psychological data.
Allows two-way communication with PAC server.
Analyzes patient data collected and delivers
pre-recorded responses and/or medication dosage
recommendations based on physician instructions
loaded in PPM.
Downloads patient data to PAC server at
specified time intervals or in real time.
Receives messages, updates to physician
instructions and prescription dosage parameters,
dosage algorithms, fixed or contingent self-
monitoring schedules, words of encouragement or
other feedback from PAC server.

Patient data collected via a PPM may include physiologic or biologic data (e.g., blood glucose measure, body temperature, urine ketones, and the like) and behavioral data (e.g., assessments related to diet, exercise, stress, the presence of illness). A PPM may also monitor patient medication intake (e.g., insulin dosage). A PPM, depending on the chronic illness of the patient, may contain software specifically designed for a particular patient's illness. For example, a PPM for a diabetes patient may contain physician-prescribed insulin dosage algorithms. A PPM designed for a diabetes patient will store blood glucose readings along with other relevant self-monitoring patient data. Blood from a pricked finger may be read on a chemically treated strip via the PPM. Automated insulin adjustment algorithms with physician-prescribed parameters are stored within each patient's PPM for real-time analysis and adjustment of a patient's insulin dosage. The PPM may be configured to make automatic adjustments to a patient's self-monitoring and treatment regimen based on patient-entered data. A PPM may also contain a database to help patients evaluate the effects of new medications on their target disease or to provide other disease-specific information to patients.

Patients are responsible for recording data within their PPMs and transmitting the data to a PAC server on a regular basis. Preferably, transmission of data to a PAC server is highly automated and substantially "hands-off" for a patient. A patient preferably can plug a PPM into a standard telephone jack and, with the press of a button, establish communications with a PAC server. Each PPM may have the ability to prompt patients when data transmissions are required, and to initiate and complete data transmissions using an alarm-driven timer.

Preferably, each PPM contains a user interface for displaying text, graphics, prompts and various other information. A PPM user interface serves as the primary means of communication between the PAC server and the patient. A PPM may also be configured to notify patients of transmission schedules to the PAC server; to notify patients having emergency medical conditions to promptly seek medical attention; and to provide motivational feedback to patients based upon past performance (e.g., reward patients for keeping on schedule with data recordings and transmissions of data to a PAC server).

Figure 2:
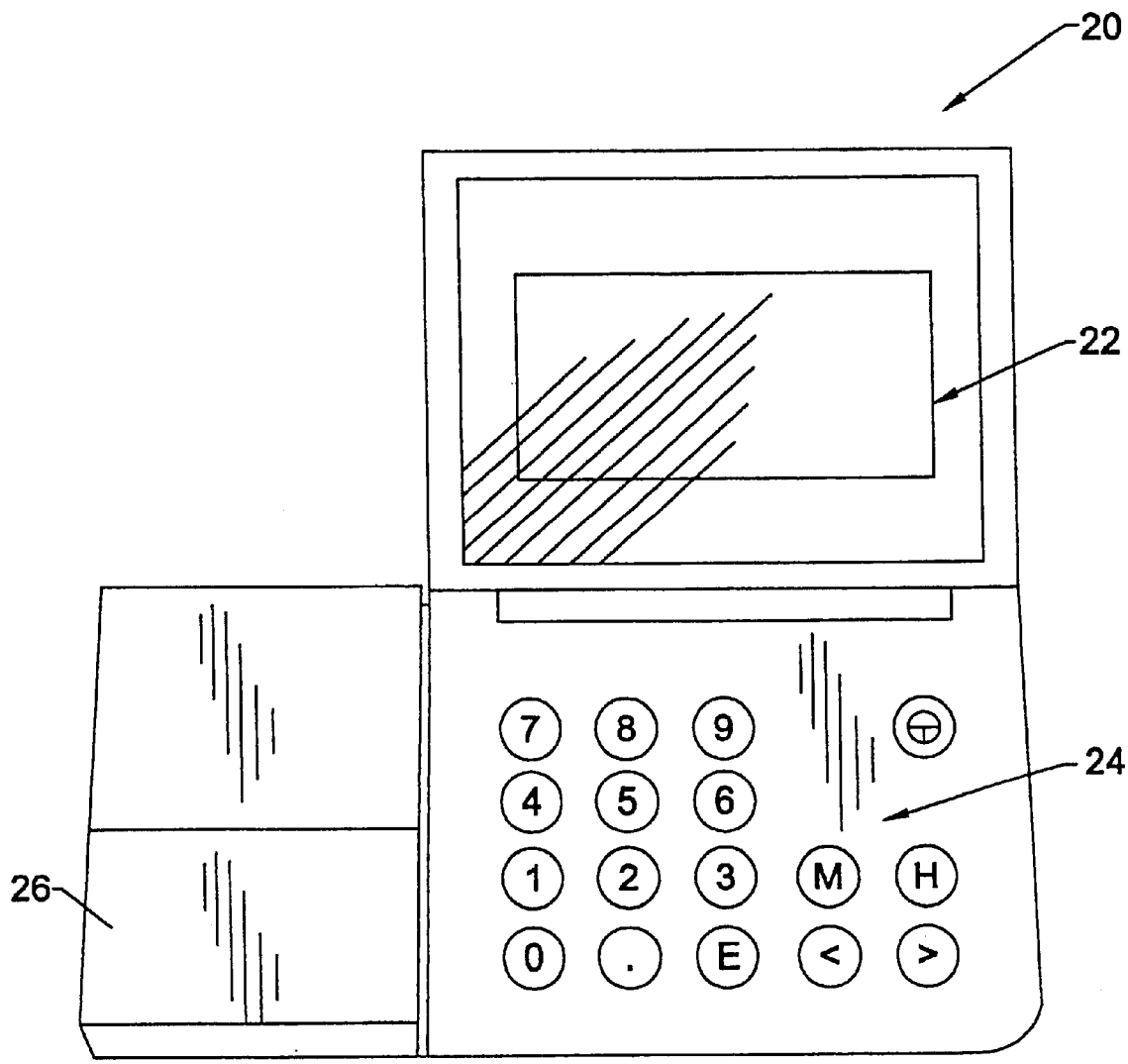
FIG. 2 illustrates an exemplary portable patient monitor (PPM).

Referring now to FIG. 2, an exemplary PPM 20 for monitoring blood glucose levels of diabetes patients is illustrated. The illustrated PPM 20 includes a display 22, a keyboard 24, and a glucose meter 26. The PPM 20 also preferably includes the following which are not shown: internal, non-volatile data storage, internally stored insulin monitoring software, and a data processor for operating the glucose meter and for communicating with a PAC server. The glucose meter 26 uses patient-entered data and internal software to continuously alter insulin doses as needed. Each time the glucose meter is used to record blood glucose values, the internal software may query the patient for various information including, but not limited to, health status, diet, exercise, and insulin taken. Preferably, the PPM internal software is menu-driven for ease-of-use by patients. Preferably, the menus are written in various languages including a children's version incorporating game-like features.

Preferably, all data entered within the glucose monitoring PPM 20 is stored with date and time information and can be alarm initiated (i.e., a patient or PPM can be prompted to perform a task or function). Preferably, the PPM internal software analyzes the entered data and continuously informs the patient of his/her prescribed insulin dose before the next injection. The PPM internal software calculates adjustments for a patient's insulin dosage according to a physician's prescription as applied to the data entered into the PPM by the patient.

Preferably, the internal software of a PPM is configurable by a case manager via a PAC server. A case manager can make adjustments to a patient's insulin dose calculations, to a patient's dosage algorithm, and to a patient's fixed or contingent self-monitoring schedules. These adjustments can be made automatically within a PPM during routine data transfer to a PAC server. In addition to providing insulin therapy management, a PPM can be used to remind patients to schedule appointments for important examinations.

An exemplary medicine dosage algorithm for use within a PPM is the Diacare® insulin adjustment algorithm by Healthware Corporation, Chapel Hill, N.C., assignees of the present invention. This insulin adjustment algorithm allows a physician to specify retrospective and/or supplemental insulin adjustment treatment regimens. The Diacare® insulin adjustment algorithm also guides a patient in "fine tuning" insulin dosage.

Preferably, a PPM contains a database of medication interaction information and is configured to allow a patient to query the database for information related to the patient's use of multiple medications. A PPM may be configured to communicate with an external database containing medication interaction information, as well. For example, a patient may query a database located within a PAC server when communications are established between the PPM and the PAC server. A PPM may also be configured to allow a patient to establish communications with other external databases, such as those residing in various legacy systems.

Other features of a PPM which are not illustrated, but which may be included, are PCMCIA slots for connecting a PPM to various peripheral devices; RJ11 connections to land line telephone systems; and infrared ports for communications with peripheral devices. Additional PPM features for diabetes patients are disclosed in U.S. Pat. No. 4,731,726 which is incorporated herein by reference in its entirety.

PPMs, according to the present invention, are not limited to land line telephone communications with a PAC server. PPMs may communicate with a PAC server using various communications technologies, without limitation. For example, a PPM may incorporate wireless communications technology for communicating with a PAC server. A PPM may also incorporate direct satellite communications technology for communicating with a PAC server.

Physician Access Center Server

Data entered into a PPM (12 of FIG. 1) by a patient is transferred to a central data processing system 14 (referred to hereinafter as a PAC server) via a telephone and modem. It is understood that a PAC server 14 may be one or more data processing devices arranged in a network. Preferably, a direct communications connection is established between a PPM 12 and a PAC server 14. Alternatively, an indirect communications connection may be established between a PPM 12 and the PAC server 14 via the Internet or other network. A communications server is preferably utilized to handle inbound and outbound communications between a PPM 12 and the PAC server 14, as would be understood by those skilled in the art of client-server communications. The term PAC server, as used herein, includes databases for storing and manipulating patient data as well as other server functions including, but not limited to web servers, application servers, e-mail servers, fax servers, AVM servers, and the like. A particularly preferred PAC server utilizes an Intel based processor running Windows NT Server 4.0 as its operating system. Preferably, a PAC server 14 is configured to handle more than 250,000 patients with at least 500 concurrent client connections. However, a PAC server 14 may be implemented using other processors and via other computing devices, including, but not limited to, mainframe computing systems and mini-computers.

A PAC server 14 analyzes and stores data transmitted from each patient PPM 12. This data is made available to authorized case managers who can access the data via a CCM 16 in TCP communication with a PAC server 14 via the Internet. In particular, a PAC server 14 identifies and prioritizes patient medical problems using the data transmitted from the patient PPMs 12. This allows case managers to focus their attention first on patients with significant medical problems.

Preferably, a PAC server 14 performs real-time analysis on data as it is being transmitted from a PPM to identify medical emergency situations that require immediate attention. If such a medical emergency is identified, a patient can be immediately notified via communications from a PAC server 14 to a PPM 12, without the intervention of a case manager. Alternatively, a case manager can be notified and the patient contacted directly via phone, e-mail, fax, or other modes of communication.

A PAC server 14 performs various other functions including allowing case managers to change the treatment program for patients, such as insulin dosage, when a patient downloads data to a PAC server 14. In addition, a PAC server may include a "tickler system" for reminding case managers to verify that communications with patients have occurred and for verifying that medical conditions requiring medical attention have been resolved. A PAC server may also be configured to track patient supply usage automatically (e.g., insulin test strips, lancets and syringes) and this information may be used to provide just-in-time delivery of replacement supplies to a patient. A PAC server may be configured to communicate with manufacturers and distributors of medical supplies utilized by patients. By monitoring patient usage of supplies, orders can be placed with manufacturers and distributors directly via a PAC server such that medical supplies can be delivered to patients.

A separate warehouse database may be added to a PAC server 14 to support complex analysis of patient data, and may also be used to review prescriptive changes made to a patient's medical regimens and medication dosages.

Case Manager Clients

As illustrated in FIG. 1, case managers access a PAC server 14 via a case manager client (CMC) 16 connected to the same network. The CMC 16 preferably communicates with a PAC server 14 using TCP/IP protocol over an Internet connection between the CMC and the PAC server. Data encryption may be utilized and other security methods may be implemented to transfer information between a PPM and PAC server and between a CMC and the PAC server or a PPM.

Exemplary devices which may serve as CMCs 16 for purposes of the present invention may include, but are not limited to, desktop computers and portable computing devices, such as personal digital assistants (PDAs). A CMC 16 preferably includes a central processing unit, a display, a pointing device, a keyboard, access to persistent data storage, and an Internet connection for connecting to the Internet 17. An Internet connection may be made via a modem connected to traditional phone lines, an ISDN link, a T1 link, a T3 link, via cable television, via an ethernet network, and the like. An Internet connection may be made via a third party, such as an "Internet Service Provider" ("ISP").

An Internet connection may be made either by a direct connection of a CMC to the Internet or indirectly via another device connected to the Internet. In the latter case, a CMC is typically connected to this device via a local or wide area network (LAN or WAN). Preferably, data transfer rates between a CMC and a PAC server are equal to, or greater than, fourteen thousand four hundred baud (14,400 baud). However, lower data transfer rates may be utilized.

Preferably, a CMC 16 has an Intel® 80486 processor (or equivalent) with at least eight megabytes (8 MB) of RAM, and at least five megabytes (5 MB) of persistent computer storage for caching. Even more preferable is an Intel® Pentium® processor (or equivalent). However, it is to be understood that various processors may be utilized to carry out the present invention without being limited to those enumerated herein. Although a color display is preferable, a black and white display or standard broadcast or cable television monitor may be used. A CMC 16, if an IBM®, or IBM-compatible personal computer, preferably utilizes either a Windows® 3.1, Windows 95®, Windows NT®, Unix®, or OS/2® operating system. However, it is to be understood that a terminal not having computational capability, such as an IBM® 3270 terminal or a network computer (NC), or having limited computational capability, such as a network PC (Net PC) may be utilized in accordance with an embodiment of the present invention for accessing the Internet in a client capacity.

Herein, the term "Internet" shall incorporate the term "computer network" such as an "Intranet", and any references to accessing the Internet shall be understood to mean accessing a hardwired computer network as well. Herein, the term "computer network" shall incorporate publicly accessible computer networks and private computer networks, and shall be understood to support modem dial-up connections.

A case manager accesses a PAC server 14 via a CMC 16 to review the medical conditions of multiple patients. Case managers preferably are able to review, via information downloaded from a PAC server 14, all patient activity and data for their assigned patients including data transmission history, prescription review, analysis and adjustment. A CMC 16 allows a case manager to review patient data in various formats, including a hierarchical, problem-oriented format wherein patients with medical conditions requiring immediate attention are presented foremost. A CMC 16 may also allow a case manager to add, edit, and delete certain patient data stored in a PAC server 14. A CMC 16 also can interface directly with each PPM 12 to provide a patient with information and to modify illness-specific software contained therein. For example, an insulin dosage algorithm contained within the internal software of a particular patient's PPM can be modified remotely by a case manager via a CMC 16.

System Security

Access to a system for monitoring, diagnosing, and treating medical conditions of remotely located patients with various chronic illnesses, according to the present invention, may be controlled using logon security which provides case managers and other users with certain circumscribed privileges to examine and/or edit data. These rights can limit certain users ability to examine confidential clinical health data, and may also be employed to limit the ability to edit any clinical data or make changes to specific fields in a patient's medication dosages or dosage adjustment algorithm. Similar access control may be applied to the data, at various levels, which define patients' medical conditions and their associated priorities and pre-emptive relationships.

Flexible configuration and associated security may be an element of a system for monitoring, diagnosing, and treating medical conditions of remotely located patients, according to the present invention, that permeates many of the subsystems. Default values and classifications for many values may be provided at the system level. Default values may be modified in a hierarchical manner, and may be controlled in part by access rights of a user, to a permit uniqueness at various levels.

Operations

Figure 3:
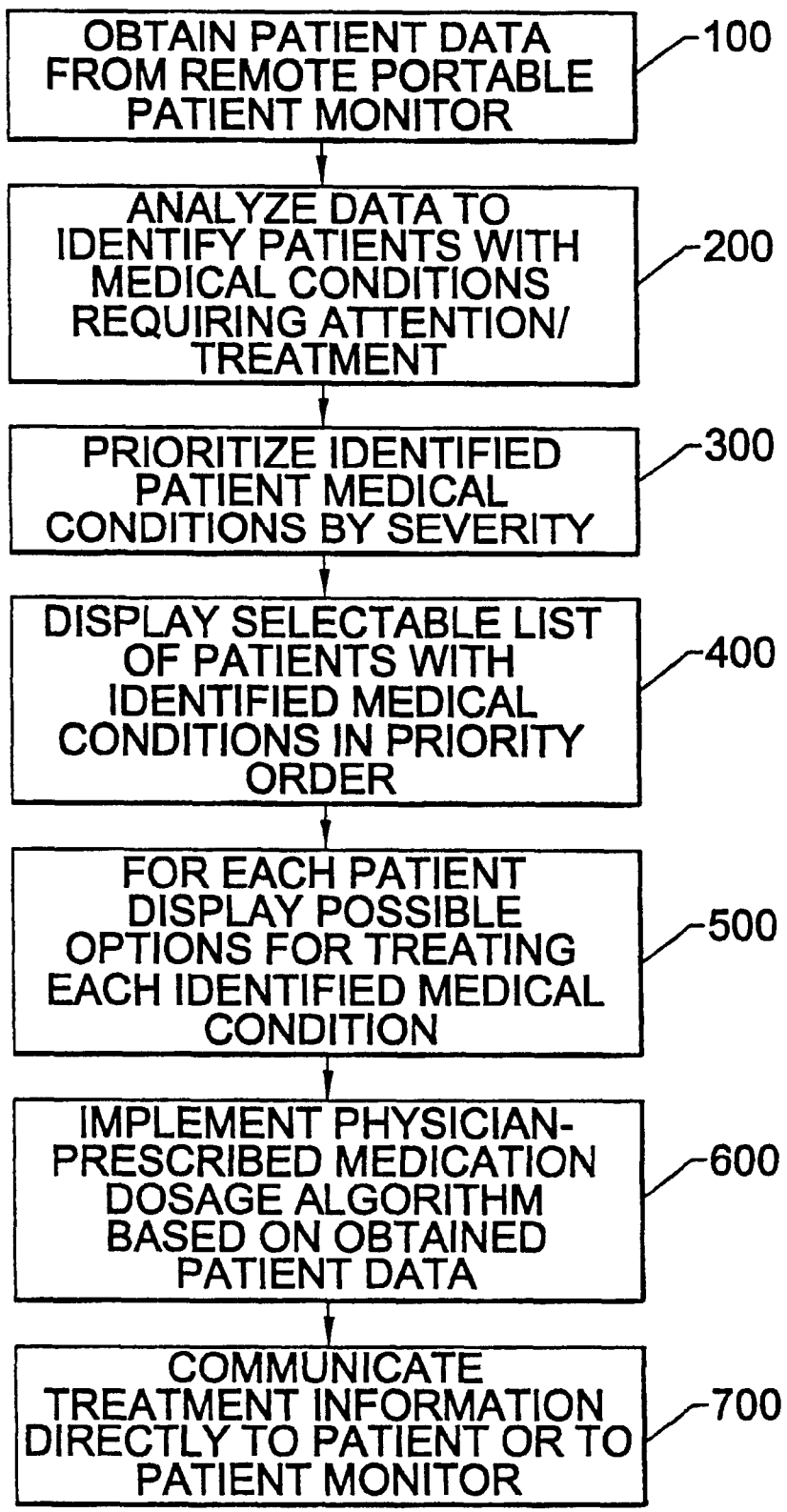
FIG. 3 schematically illustrates operations for monitoring, diagnosing and treating medical conditions of a plurality of remotely located patients according to the present invention.

Referring now to FIG. 3, operations for monitoring, identifying, prioritizing and treating medical conditions of patients with chronic illnesses, according to the present invention, are schematically illustrated. Patient data are obtained by a PAC server from a PPM (Block 100). A PAC server analyzes the obtained data to identify patients with medical conditions requiring treatment or some type of medical attention (Block 200). A PAC server prioritizes the identified patient conditions according to medical severity (Block 300). A PAC server displays to a case manager (or other user), via a client in communication with the PAC server, a selectable list of patients with identified medical conditions arranged in priority order (Block 400). A PAC server provides to a case manager, via a client, options for treating each identified medical condition (Block 500). Physician-prescribed medication dosage algorithms may be implemented based on patient data obtained from a PPM (Block 600). Treatment information may be communicated directly to a patient or to a patient's PPM by a case manager via a client in communication with a central data processing system (Block 700). The operations set forth in FIG. 3 are described in detail below.

Obtaining Data From PPM

Figure 4:
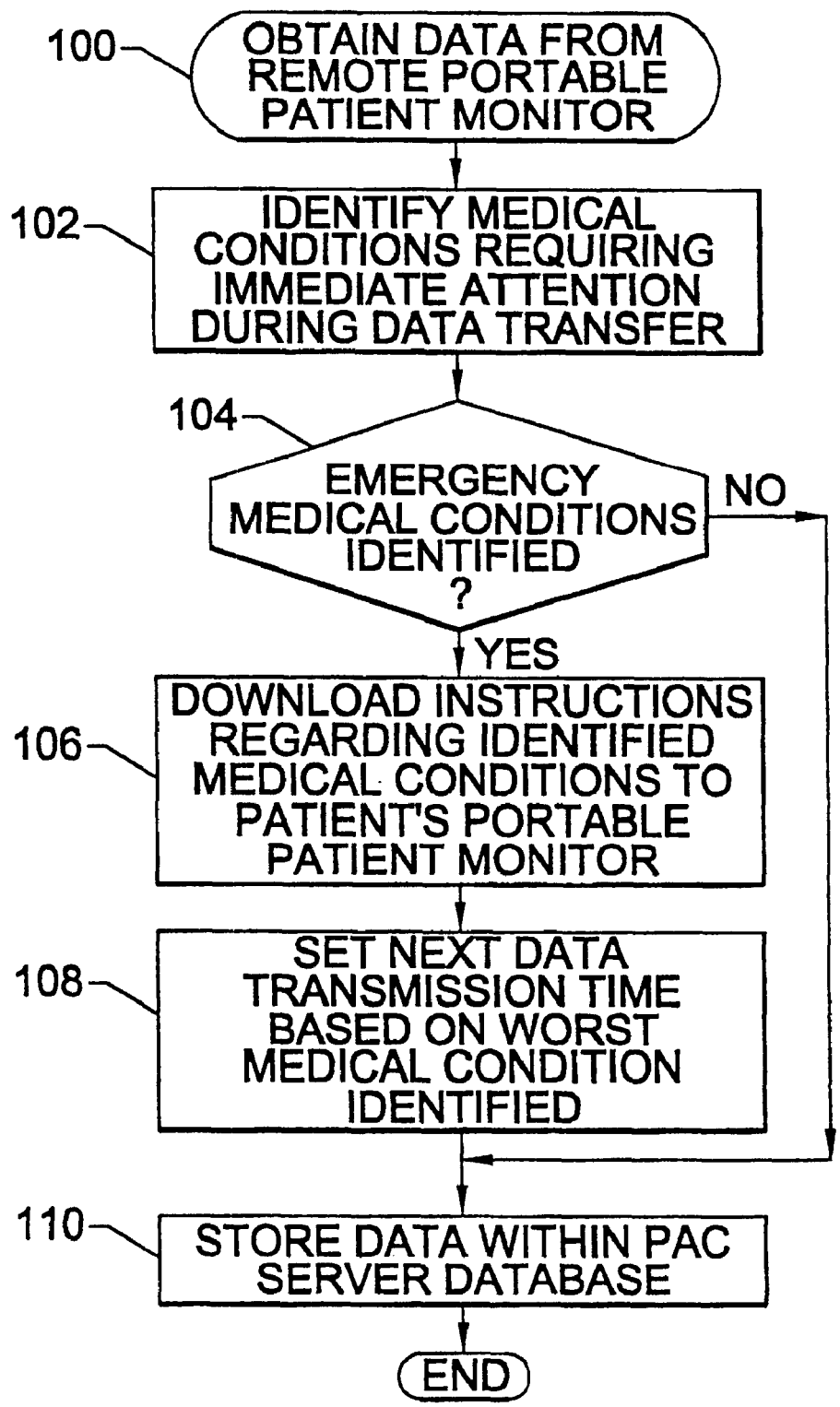
FIG. 4 schematically illustrates operations for obtaining data from a remotely located patient monitoring device.

In a preferred embodiment, when a PAC server obtains patient data from a PPM (Block 100), operations schematically illustrated in FIG. 4 may be performed. Preferably, data transmitted to a PAC server is analyzed substantially simultaneously with transmission of the data for the purposes of identifying "emergency" medical conditions requiring immediate medical attention (Block 102). Preferably, this analysis is performed while communications are still established between a PAC server and a PPM transmitting the data. If emergency medical conditions are not identified (Block 104), data obtained from a PPM is stored within a PAC server database for later analysis and retrieval (Block 110).

If emergency medical conditions are identified (Block 104), instructions are downloaded to the PPM regarding what actions should be taken by the patient (Block 106). For example, the patient may be instructed to immediately take a specific medication or to immediately seek medical attention. If a medication dosage algorithm is stored in a PAC server, the PAC server may communicate a new medication dose to the PPM, or to the patient via telephone, AVM, e-mail, facsimile transmission, and the like. In addition, changes may also be made to medicine dosage algorithms stored within a PPM or within the PAC server, such that a patient's next dose of medicine is changed in response to the identified emergency medical condition. Furthermore, changes may also be made to a patient's fixed or contingent self-monitoring schedules. The next scheduled time for data transmission from the PPM to the PAC server may be set, based on an identified medical condition's severity, such that higher condition severities result in more frequently scheduled transmissions (Block 108). For example, PPMs for patients with urine ketones may be reprogrammed to transmit every 12 hours, while PPMs for patients with high glucose may be adjusted to transmit every 3 days, while patients with no identified conditions may transmit on a routine schedule such as every week. The data obtained from a PPM is then stored within a PAC server database for later analysis and retrieval (Block 110).

Figure 5:
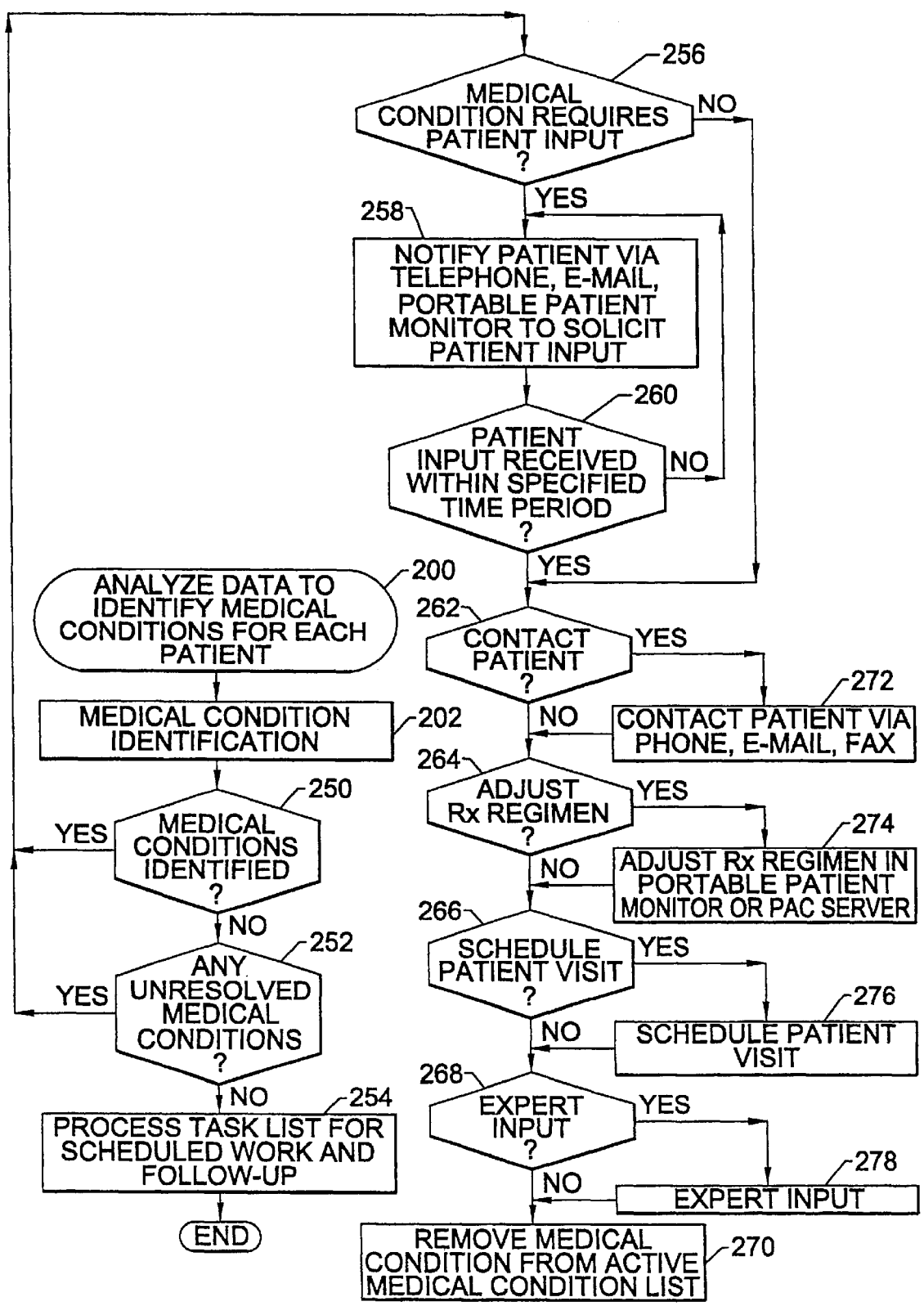
FIG. 5 schematically illustrates operations for analyzing data to identify medical conditions of a remotely located patient.
Figure 6:
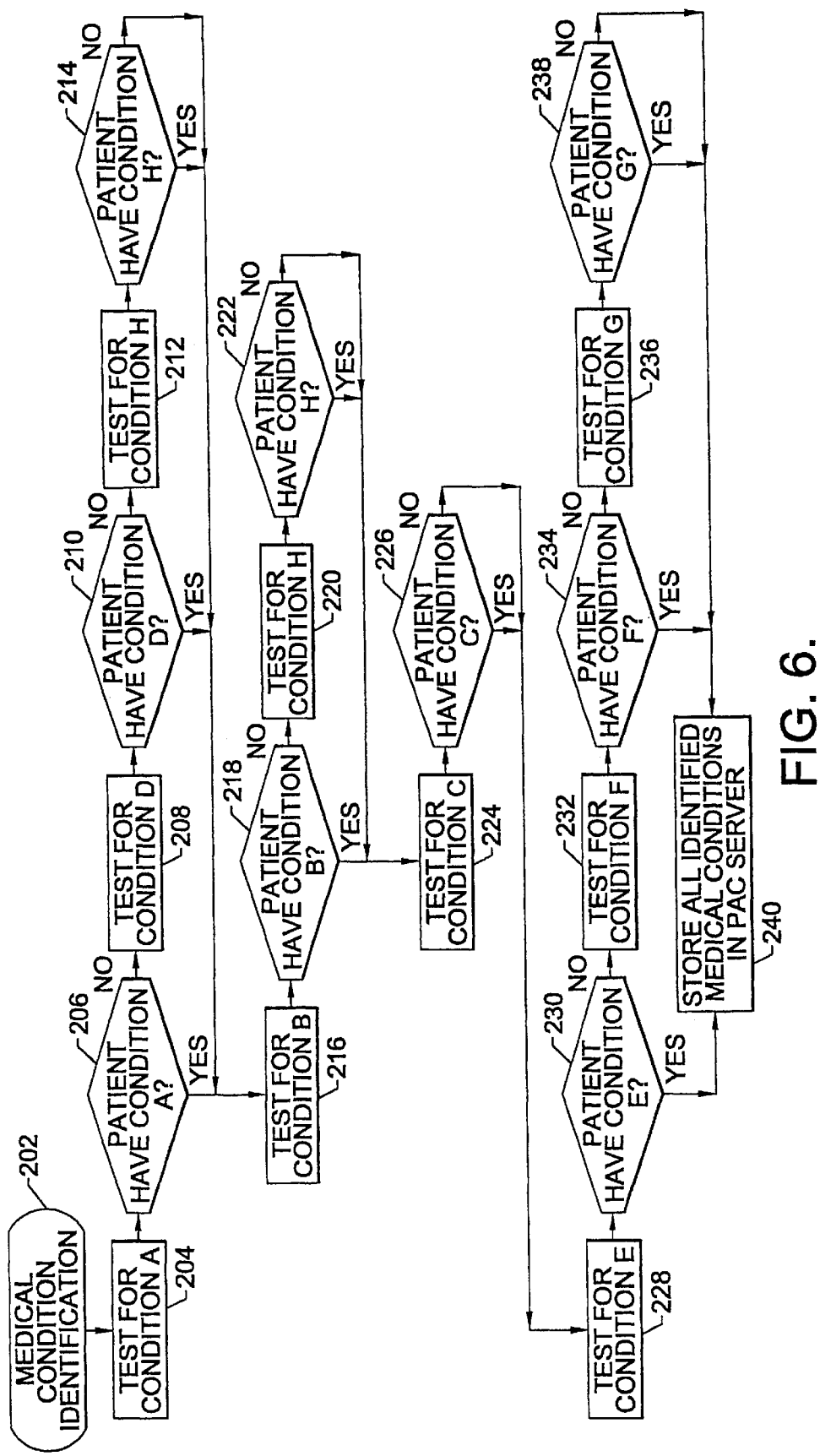
FIG. 6 schematically illustrates operations for identifying medical conditions according to aspects of the present invention.

Analyzing Patient Data to Identify Patients With Medical Conditions Requiring Medical Attention or Treatment Referring now to FIG. 5, preferred operations for analyzing patient data transmitted from a PPM to a PAC server to identify medical conditions requiring medical attention or treatment are schematically illustrated. Initially, operations for identifying medical conditions from transmitted data (Block 202) are performed. Exemplary operations represented by Block 202 are schematically illustrated in FIG. 6, and are discussed below.

Still referring to FIG. 5, if medical conditions requiring attention are not identified from data transmitted from a PPM (Block 250), a determination is made whether there are any unresolved medical conditions for the patient requiring attention or treatment (Block 252). If there are no unresolved medical conditions, case managers may provide patients with positive feedback to reinforce their self-monitoring practices and encourage continued compliance with the treatment regimen(s) (Block 254). Additionally, patients with chronic diseases must have regularly scheduled reviews and assessments, with the latter performed predominantly in the clinic. Periodic comprehensive reviews of the patients can be performed and may utilize all available inputs, including the most recent month's PPM data. These periodic assessments may be flexibly scheduled depending upon the disease and/or disease state of individual patients. These reviews provide a structured means by which the case manager may work to optimize care for patients who otherwise are not specifically identified as having medical conditions that require treatment, but who nonetheless can benefit by feedback and further optimization of medication doses, algorithmic methods for adjusting doses, self-monitoring schedule and by coordinating medical assessments and procedure conducted by other medical specialists (e.g., patients with diabetes require periodic eye and food exams, and may require consultations with dieticians.

If medical conditions are identified (Block 250) from transmitted data from a PPM, or if there are unresolved medical conditions for the patient (Block 252), a determination is made whether a medical condition requires additional patient input (Block 256). If patient input is required, the patient is notified by various methods, such as via telephone, e-mail, AVM, facsimile transmission, or via the patient's PPM (Block 258). Preferably, the present invention includes a "tickler" system for monitoring whether a patient provides required input within a specified time period (Block 260). If a patient does not provide required input within a specified time period, the present invention may prompt a case manager to re-notify a patient of required input (Block 258).

If input from a patient is not required (Block 256) or if patient input has been received (Block 260), a case manager is provided with various options for resolving one or more medical conditions. A case manager may be presented with an option to contact a patient (Block 262). If a case manager decides to contact a patient, the present invention facilitates communication via telephone, e-mail, AVM and facsimile transmission (Block 272). A case manager may be presented with an option to adjust a medicine dosage algorithm, a patient's dosage, or a patient's fixed or contingent self-monitoring schedule, either within a patient's PPM or the PAC server (Block 264). If a case manager decides to adjust a medicine dosage algorithm within a patient's PPM, the present invention facilitates this modification though a PAC server the next time communications are established between the PAC server and the patient's PPM (Block 274). A patient may be prompted to establish communications between his/her PPM and a PAC server to receive modifications made by a case manager. Alternatively, if a medicine dosage algorithm resides within a PAC server, a case manager can instruct the PAC server to adjust medicine dosage and transmit this information to the patient.

In addition, a case manager may be presented with an option to schedule a patient for a visit with a health care provider (Block 266) or with an option to seek expert medical input (Block 268). If these options are selected, the present invention facilitates scheduling a patient to visit a health care provider (Block 276) or obtaining input from a medical expert (Block 278). A case manager may decide that no action is required for a particular medical condition and may remove an identified medical condition from an active medical condition list for a particular patient after reviewing available data (Block 270).

Referring now to FIG. 6, exemplary operations performed by a PAC server for identifying medical conditions requiring medical attention or treatment are schematically illustrated. Preferably, these operations are performed by a PAC server immediately after transmission of data from a PPM to the PAC server. For any given chronic disease, there may be relationships between medical conditions that a patient may have. For example, a patient afflicted with diabetes mellitus may exhibit two medical conditions having differing degrees of medical severity. One medical condition may have a high degree of medical severity requiring immediate attention. The other medical condition may have a much lower priority and may not require immediate medical attention. When multiple medical conditions are identified, two or more of these conditions for a given patient may represent problems of a similar type (e.g., elevated blood sugar) which differ only in severity (as defined by the system implementation). Conditions of lesser severity of the same type may be ignored (if identified) or may not be identified in the first place, if a condition of the same type at a higher priority has already been identified. It is presumed that identification and treatment of the most severe condition identified will obviate the needs to identify or treatment less severe conditions of the same type. Two methods are presented for achieving this aim below.

The present invention facilitates identifying and addressing medical conditions having the highest degree of medical severity first by organizing possible medical conditions for a given chronic disease into various classifications and by prioritizing medical conditions within each classification. Classification and prioritization within classes are illustrated below with respect to Table 2.

TABLE 2

| CLASS | MEDICAL CONDITION | PRIORITY | SUB_PRIORITY |
| --- | --- | --- | --- |
| 1 | A | 1 | A |
| 1 | A | 1 | B |
| 1 | A | 1 | D |
| 1 | A | 1 | L |

TABLE 2-continued

| CLASS | MEDICAL CONDITION | PRIORITY | SUB_PRIORITY |
|---|---|---|---|
| 1 | A | 1 | Q |
| 1 | B | 2 | A |
| 1 | B | 2 | D |
| 1 | B | 2 | F |
| 1 | B | 2 | M |
| 1 | B | 2 | Q |
| 1 | B | 2 | Z |
| 1 | C | 3 | A |
| 1 | C | 3 | B |
| 1 | C | 3 | S |
| 1 | C | 3 | U |
| 2 | D | 1 | A |
| 2 | D | 1 | B |
| 2 | D | 1 | C |
| 2 | D | 1 | F |
| 2 | E | 2 | A |
| 2 | E | 2 | C |
| 2 | E | 2 | F |
| 2 | F | 3 | A |
| 2 | F | 3 | D |
| 2 | F | 3 | F |
| 2 | F | 3 | Z |
| 3 | G | 1 | A |
| 3 | G | 1 | B |
| 3 | G | 1 | D |
| 3 | H | 2 | A |
| 3 | H | 2 | B |
| 3 | H | 2 | C |
| 3 | H | 2 | D |

The column entitled Sub_Priority presents medical conditions within each unique combination of class and medical condition (already sorted by priority with a class) in a sorted order that is defined expressly for each combination. That is, sub_priority provides a means by which the conditions in the list can be further sorted to provide additional information related to urgency. For example, problems related to late data transmissions (all within one class and assigned to have one priority) may be displayed in the order of the most overdue first. Subpriorities for each medical condition will be uniquely defined for that condition. In this example, the column labeled sub_priority may be conceived of as representing a "priority score" that can be defined for each condition. Other embodiments may utilize different methods to achieve similar means, and the process of prioritization could also be extended to additional levels as needed (i.e, sub-sub-priorities). Use of a single sub_priority column will support this feature.

Using Table 2, a relationship table may be derived to determine which medical conditions have a higher degree of medical severity than other medical conditions. An exemplary relationship table is illustrated below as Table 3. Conditions may be overridden that are either 1) unrelated but of a lesser priority than those in the first column, or 2) closely related or being of the same "type" (e.g., high blood sugar conditions) and therefore need not be identified and treated since treatment for the most severe form will obviate the need for treatment of less severe conditions of the same type.

TABLE 3

| Medical Condition | Overrides Medical Condition |
|---|---|
| A | D and H |
| B | G |
| D | H |
| E | F and G |

Referring back to FIG. 6, operations for identifying medical conditions (Block 202) based upon Table 2 and Table 3 above are schematically illustrated. Initially a test is performed for medical condition A (Block 204). If transmitted data from a PPM indicates that a patient has medical condition A (Block 206), then tests for medical conditions D and H (Block 208—Block 214) are not performed because medical conditions D and H have lower priority than medical condition A. If transmitted data from a PPM indicates that a patient does not have medical condition A (Block 206), a test for medical condition D is performed (Block 208). If transmitted data from a PPM indicates that a patient has medical condition D (Block 210), then tests for medical condition H (Block 212—Block 214) are not performed because medical condition H has lower priority than medical condition D. If transmitted data from a PPM indicates that a patient does not have medical condition D (Block 210), a test for medical condition H is performed (Block 214).

Whether or not transmitted data from a PPM indicates that a patient has medical condition H (Block 210) or if a patient has medical condition A (Block 206), a test for medical condition B is performed (Block 216). If transmitted data from a PPM indicates that a patient has medical condition B (Block 218), then tests for medical condition H (Block 220—Block 222) are not performed because medical condition H has lower priority than medical condition B. If transmitted data from a PPM indicates that a patient does not have medical condition B (Block 218), a test for medical condition H is performed (Block 220).

Whether or not transmitted data from a PPM indicates that a patient has medical condition H (Block 222) or if a patient has medical condition B (Block 218), a test for medical condition C is performed (Block 224). Whether or not transmitted data from a PPM indicates that a patient has medical condition C (Block 226), a test for medical condition E is performed (Block 228).

If transmitted data from a PPM indicates that a patient has medical condition E (Block 230), then tests for medical conditions F and G (Block 232—Block 238) are not performed because medical conditions F and G have lower priority than medical condition E. If transmitted data from a PPM indicates that a patient does not have medical condition E (Block 230), a test for medical condition F is performed (Block 232). If transmitted data from a PPM indicates that a patient has medical condition F (Block 234), then tests for medical condition G (Block 236—Block 238) are not performed because medical condition G has lower priority than medical condition F. If transmitted data from a PPM indicates that a patient does not have medical condition F (Block 234), a test for medical condition G is performed (Block 238). All medical conditions identified are then stored within a PAC server (Block 240).

By way of example, patients having condition A, identified here as high blood sugar with urine ketones, do not require treatment for, or even identification of, problems related to condition D, high blood sugar without urine ketones, or for condition H, poor control characterized by chronic high blood sugar (of lesser severity than condition D). Similarly, patients who have been identified with condition B, in this case assisted hypoglycemia, need not be screened for infrequent monitoring since the monitoring that is being conducted is picking up on a a much more severe condition. It should be further noted that the definition and specification of these medical conditions and their associated priorities, and of the relationship between conditions where the treatment and identification of lower priority condition may be superceded by those of higher priority is configurable. The problem definitions may be configured in part to reflect individual patient differences by adjustment of the default physiologic or behavioral parameters which will trigger the identification of a given problems. Where default values for identification are utilized, patient parameters are inherited from the doctor, and these may in turn be inherited from other, higher levels within the system.

Prioritizing Identified Patient Medical Conditions

According to a preferred embodiment of the present invention, identified patient medical conditions are prioritized based on a hierarchy of medical severity. In general, three classes of medical conditions (Class I, II and III) may be utilized. However, it is to be understood that various numbers and types of classes of medical conditions may be utilized without departing from the spirit and intent of the present invention.

Class I medical conditions are those that require immediate attention based on physiologic or behavioral data collected by a PPM. Although identified by a PAC server, many of these conditions may also be identified by a PPM and may result in prompts to the patient to transmit to a PAC server up-to-date data and to follow this up with a telephone call to the case manager or physician. The following are exemplary Class I medical conditions related to diabetes treatment: unexplained hypoglycemia requiring assistance from others, urine ketones with or without high blood glucose and the failure to transmit data within 24 hours after receiving notification from a PAC server that an expected transmission is late. While late transmissions may not necessarily require immediate action, they may be placed in the Class I category for reasons of health safety.

Class II medical conditions may be significant medical conditions, but may not require immediate medical attention or action on the part of a case manager. Class II medical conditions, if not addressed, may develop into Class I medical conditions that do require immediate attention. In order of decreasing severity for diabetes, Class II problems may include: explained assisted hypoglycemia, hypoglycemia; high blood glucose (BG) without urine ketones; and persistent poor control.

Class III medical conditions are defined as suboptimal conditions in which room for patient improvement may be indicated by physiologic and/or behavioral data collected from a patient's PPM. Many Class III medical conditions may relate to poor or inconsistent compliance with a self-monitoring regimen.

Figure 7:
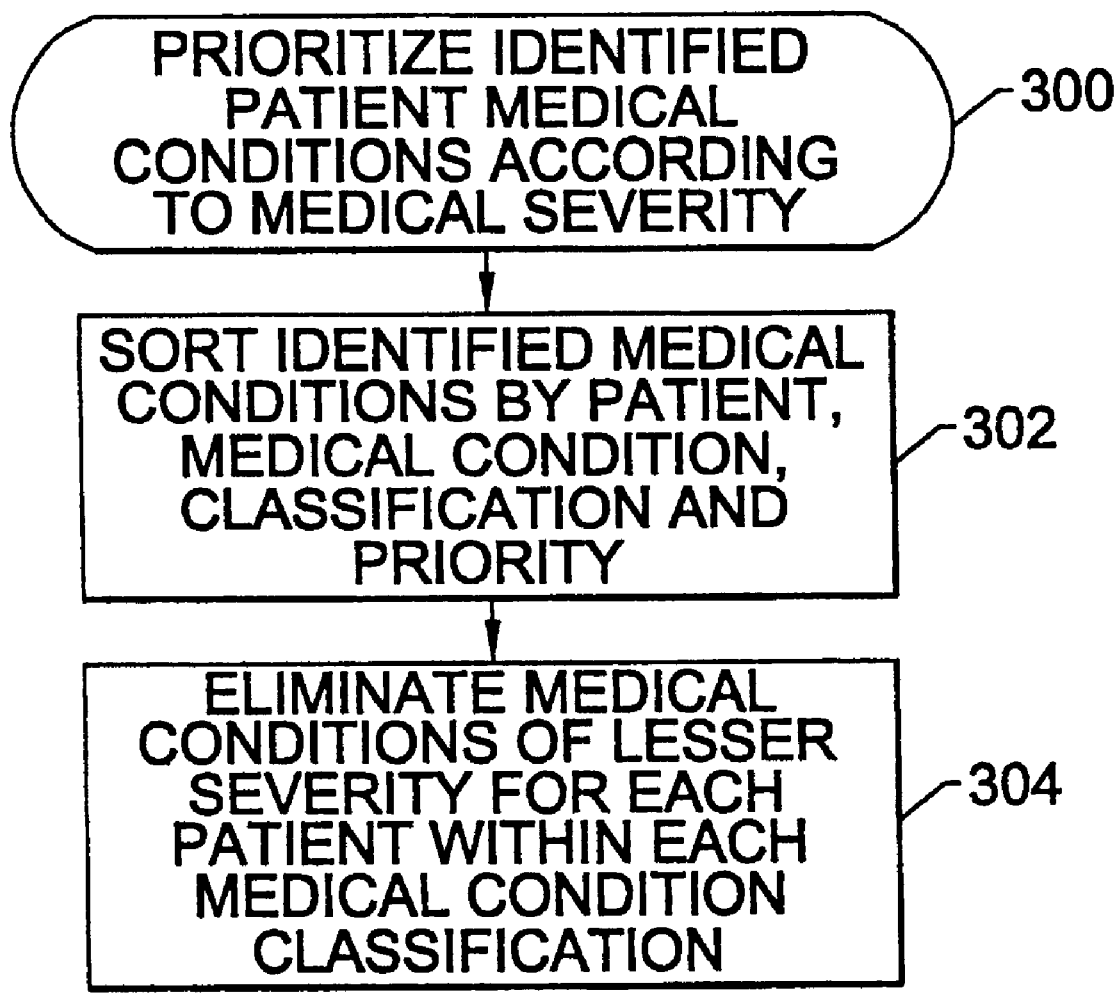
FIG. 7 schematically illustrates operations for prioritizing identified medical conditions according to aspects of the present invention.

Referring now to FIG. 7, operations for prioritizing identified medical conditions according to aspects of the present invention are schematically illustrated. Identified medical conditions are sorted by patient, medical condition, classification, priority and sub-priorities (Block 302). Medical conditions of lesser severity for each patient within each medical condition classification are eliminated (Block 304).

Figure 8:
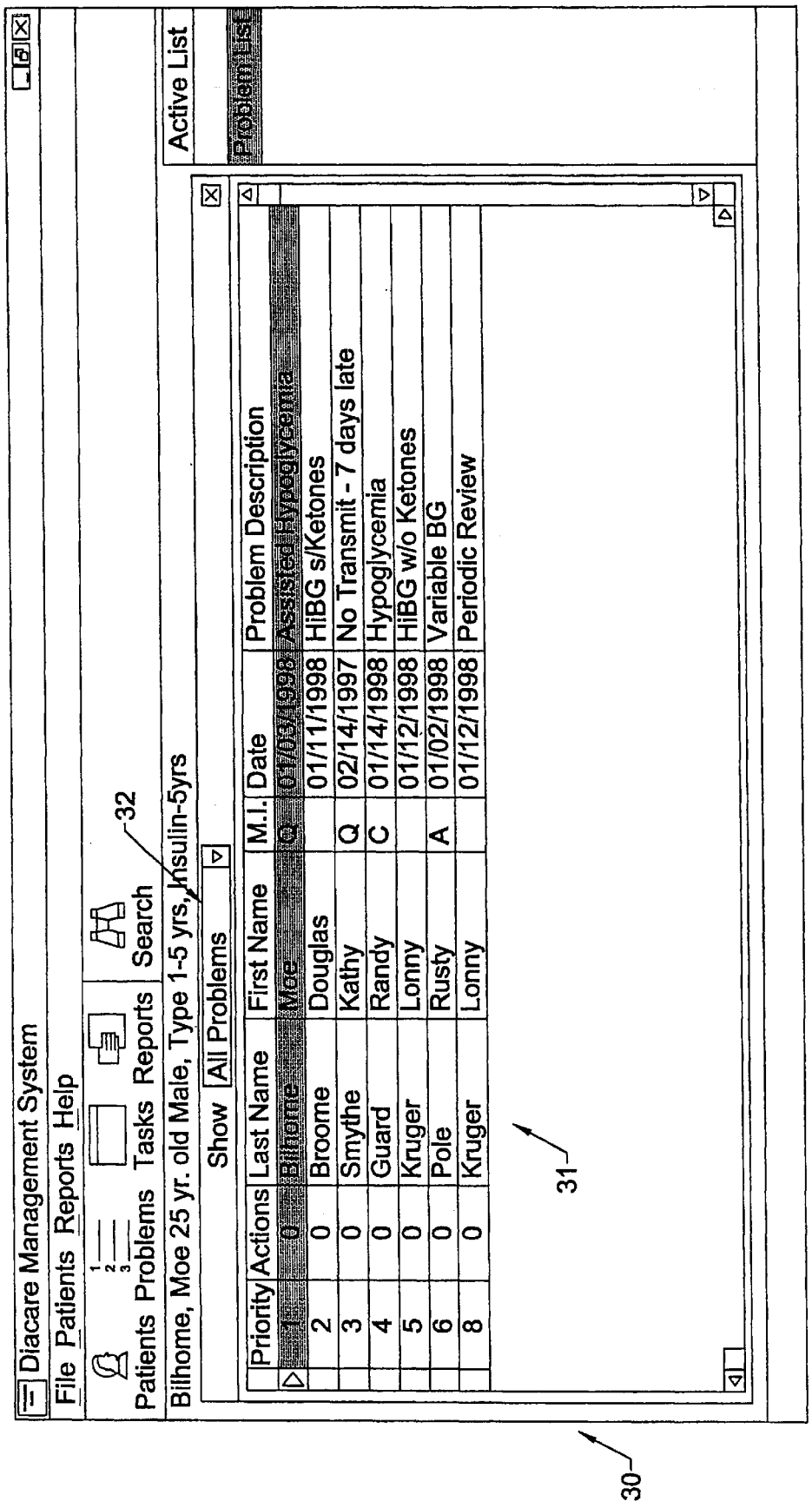
FIG. 8 illustrates an exemplary user interface for displaying medical conditions prioritized according to medical severity.

Displaying Selectable List of Patients With Identified Problems in Priority Order After all medical conditions have been identified, a list of medical conditions for each patient is normalized to eliminate medical conditions of the same type or of lesser severity. Only the remaining medical conditions for a given patient are available for display in a larger list(s) of medical conditions identified for all patients. FIG. 8 illustrates an exemplary user interface 30 wherein a list 31 of medical conditions for a plurality of patients is displayed in priority order. In the illustrated user interface 30, the patient with the highest priority medical condition is listed first. A filter allows a user (case manager) to display various levels of detail of prioritized medical conditions. A box 32 is provided in the illustrated user interface 30 that allows a case manager to select the level of displayed detail. In the illustrated user interface, the filter selection in box 32 allows all identified, prioritized medical conditions of all patients to be displayed.

A list of prioritized medical conditions appears when a case manager first logs into a PAC server via a CMC. The order of presentation is based on medical condition class. Within each class, medical conditions of different types are sorted by an assigned priority. Within each separate medical condition the individual cases are optionally sorted by a severity index. This feature may be defined separately for each type of medical condition, and further may reflect settings that are defined for individual patients as necessary or desirable. For example, late transmissions may be sorted by the number of days overdue, and persistent poor control might be sorted by the average glucose level which is chronically elevated.

Figure 9:
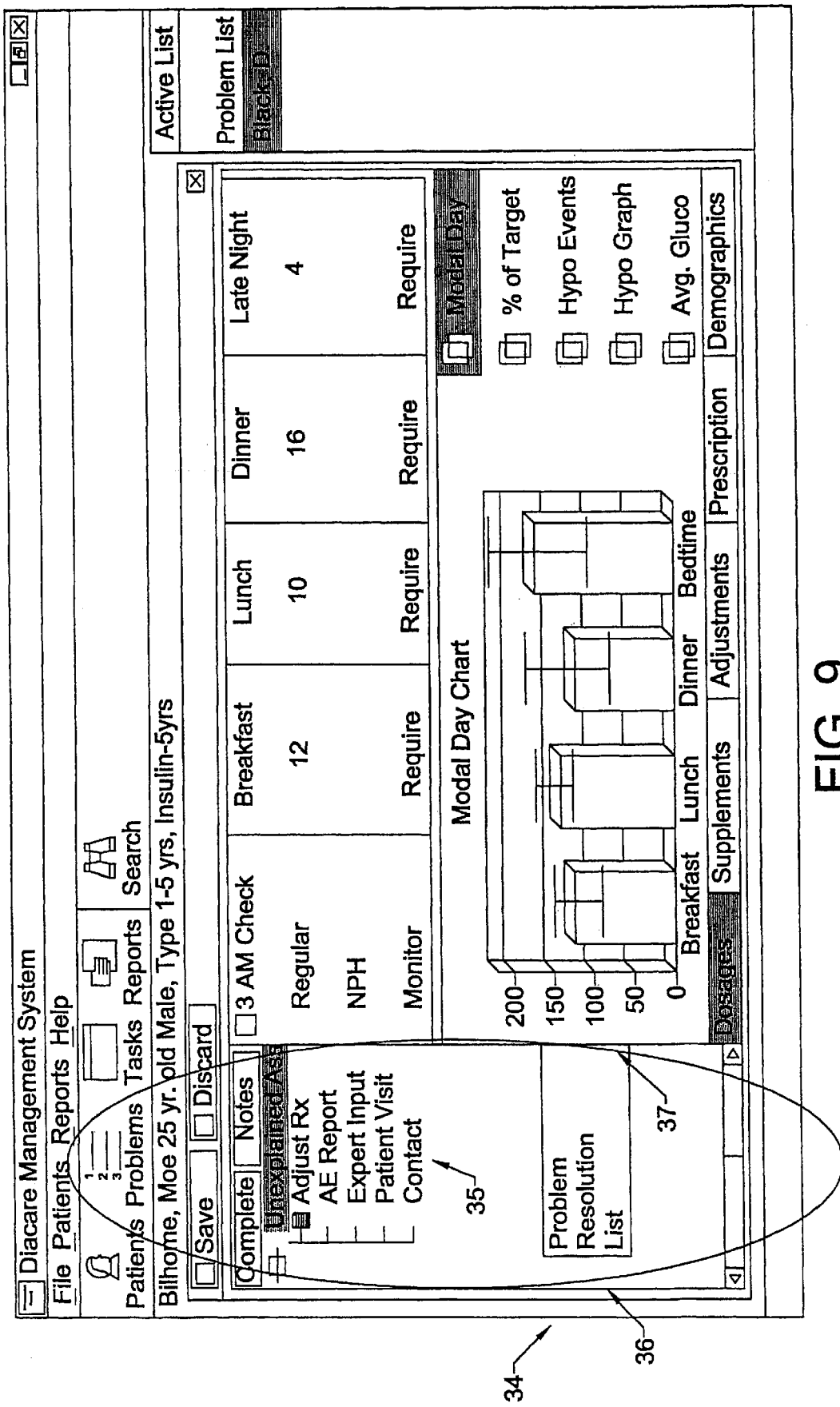
FIG. 9 illustrates an exemplary user interface for displaying patient-specific information.

Preferably, medical conditions having the highest medical severity appear at the top of the list. Selection of a patient medical condition, such as by mouse click, results in a change of the user interface to one focused upon the selected patient, as illustrated in FIG. 9. In the illustrated interface user 34 of FIG. 9, all current medical conditions 35 for the selected patient appear on the left side 36 of the user interface 34 in a list format resembling a directory structure, and the right side 37 of the user interface contains current prescriptive and report data. The listing on the left side resembles a directory structure in form and function, whereby selection of a condition by mouse click will expand the list on the left side to reveal available treatment options for the selected condition. On the right side default screens are available in a tabbed format that can be used to modify medication dosages, parameters related to the adjustment of medication in the PPM, and the fixed and contingent self-monitoring schedule. Changes to these parameters can be directly communicated to the PPM and are summarized in documentary form in a Chart Summary Report. This report and the changed data can also be used, in part, to generate AVM using text to speech technology that verbally summarizes new treatment instruction for the patient. Certain actions or treatment options which may appear below current medical conditions identified for this patient may cause other user windows and dialog boxes to appear, as described below.

Providing Options for Treating Identified Medical Conditions

The selection of a patient medical condition in the user interface of FIG. 9 by mouse click may result in an expanded list of available actions that may be taken for the chosen medical condition. The actions displayed may be only those which have been associated with the specifically-defined (and "expanded") medical condition. Selection of an action for a given medical condition may provide immediate access to user interfaces where dosages or algorithmic alterations can be made (if applicable), or may provide methods for contacting patients.

Communicating Treatment Information to Patient

A variety of specific actions may be undertaken which involve or utilize a patient's PPM. These may include the adjustment of medication dosage level or the timing for administration; adjustment of the rules or algorithmic parameters which a PPM or PAC server uses to independently adjust and alter medication dosage (e.g., alteration of the target range for the physiologic function being monitoring); alteration of the patient's self-monitoring schedule; or alteration of the parameters that trigger additional or contingent self-monitoring suggestions in the PPM (e.g., the level of glucose at which a PPM suggests that a patient test for urine ketones). In addition to these parameters, a case manager may also select and/or compose messages to be downloaded to a patient's PPM, or transmitted via telephone, AVM, e-mail and facsimile transmission, which are designed to reinforce correct behaviors or alter maladaptive behaviors. A case manager may also compose a message asking a patient to schedule an office visit with a physician, and may also alter a PPM's transmission schedule (which may take affect following the next transmission). Special messages related to scheduling office appointments ask the patient to make an appointment with a named professional and provide his or her phone number. The PPM may query the patient on a daily basis concerning whether the appointment has been made, and then solicit the appointment date for uploading to the PAC. After the appointment date has passed, the PPM can query the patient to ascertain if the appointment was actually kept.

Preferably, screening mechanisms are provided for ensuring that treatment or information provided by a case manager is medically sound for a particular patient before the treatment or information is communicated to a patient or to a patient's PPM.

Figure 10A:
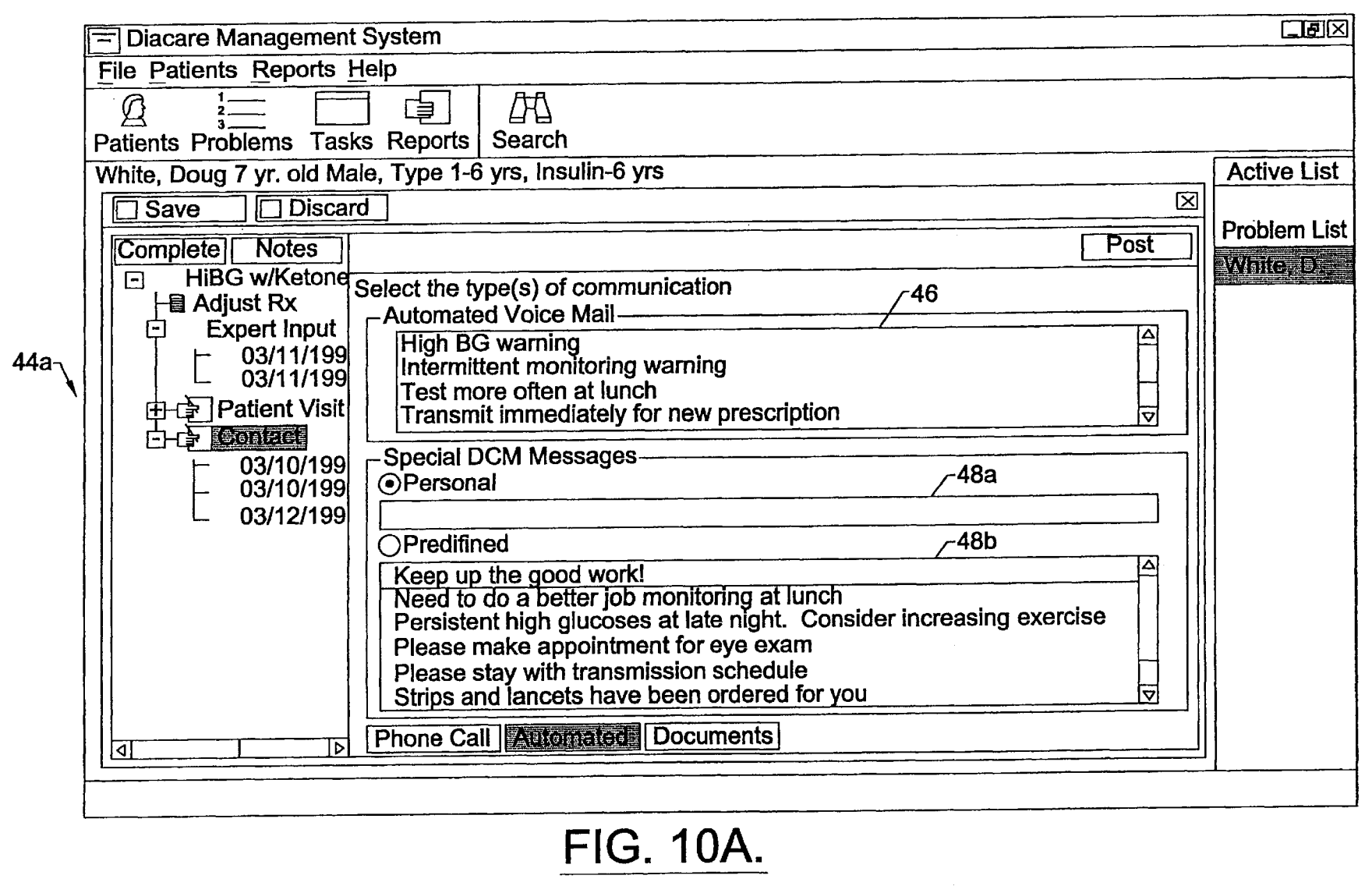
Figure 10B:
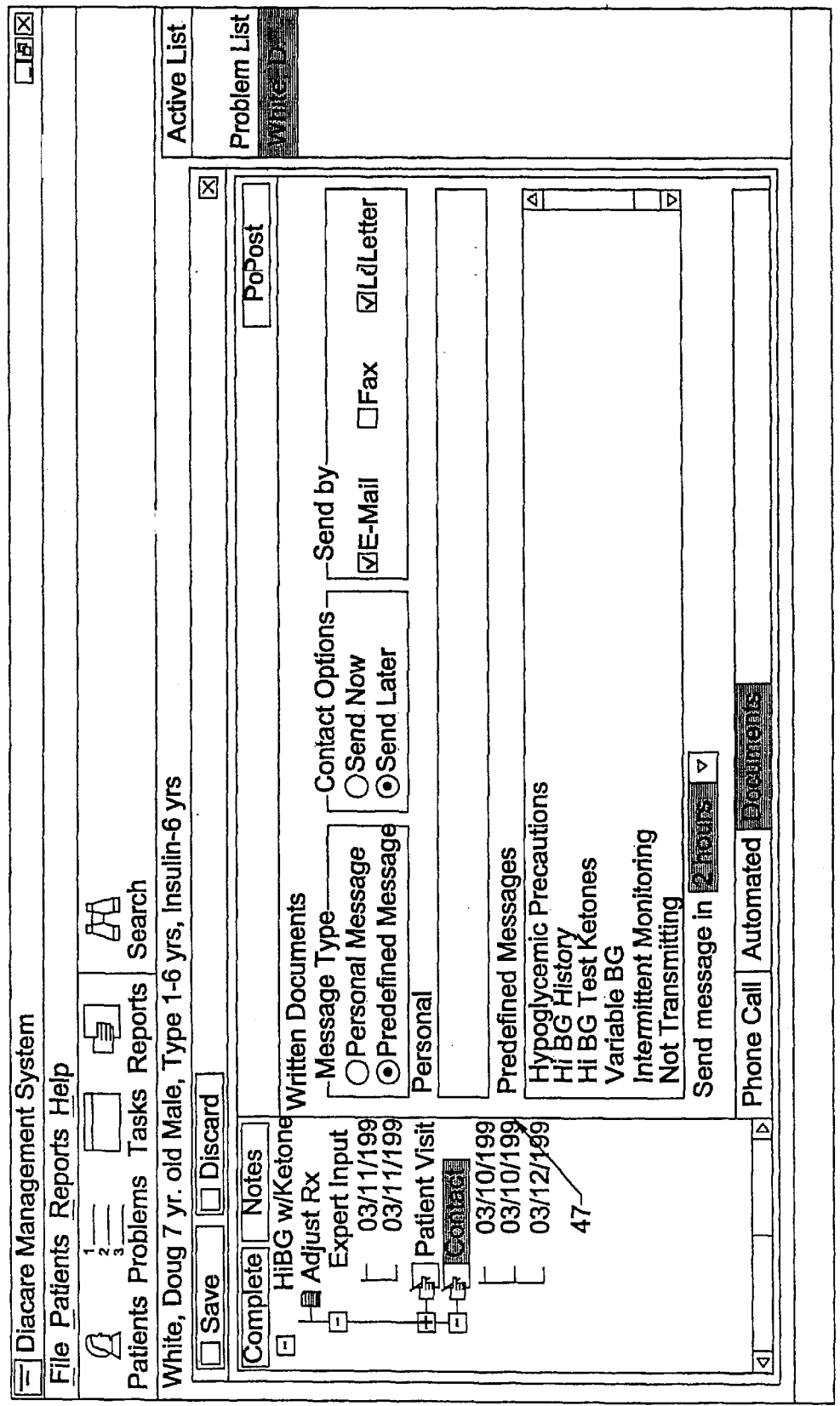
Figure 10C:
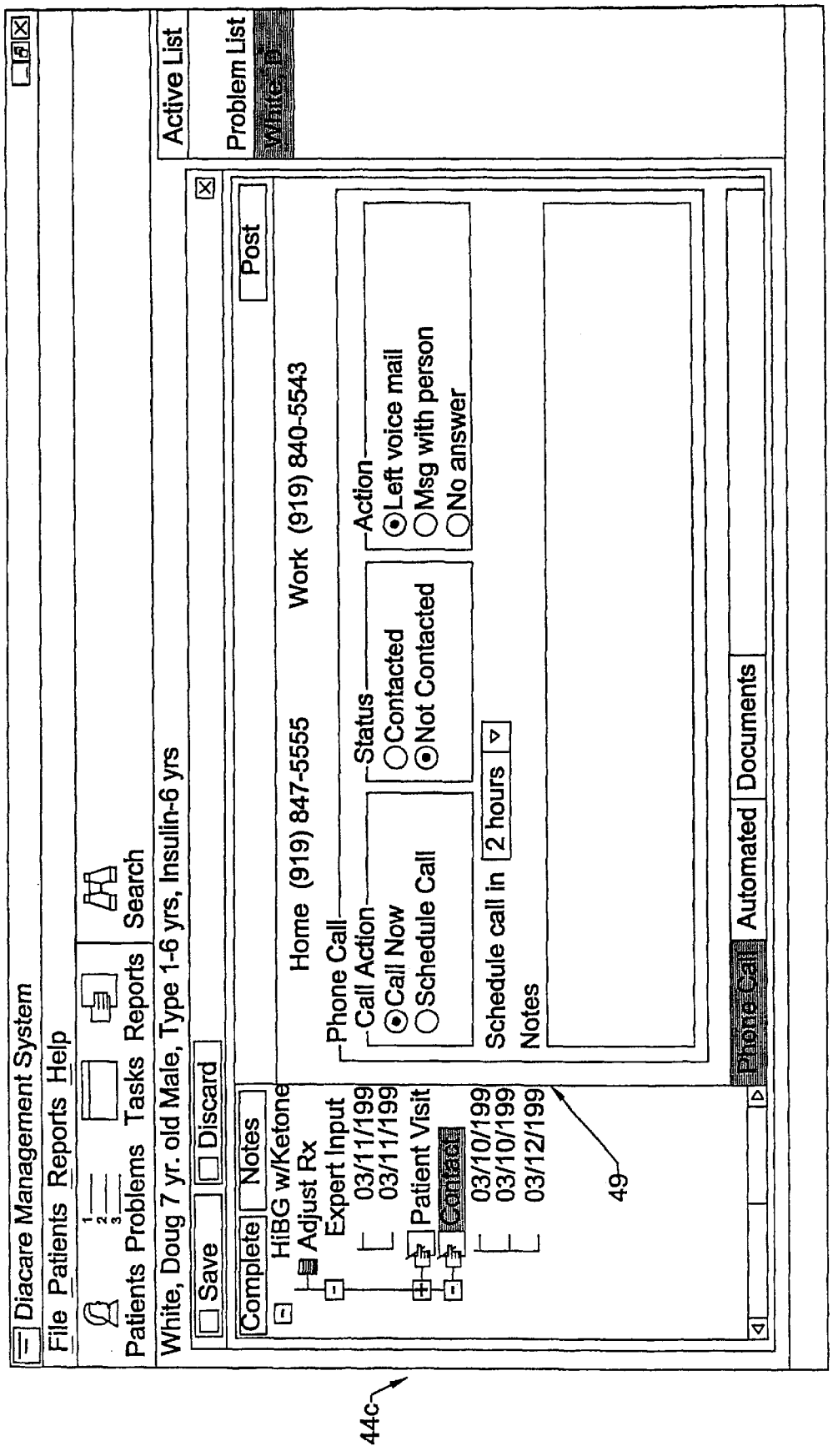

Exemplary user interfaces 44a, 44b, 44c for communicating with a patient, are illustrated in FIGS. 10A–10C, respectively. In FIG. 10A, automated voice mail (AVM) messages can be selected and sent to a patient via the box 46. In addition, personal and predefined messages can be created and/or selected via boxes 48a and 48b, respectively, and transmitted directly to a patient's PPM. In FIG. 10B, various written documents can be selected and sent to a patient via the box 47. These notices can be sent via letter, fax, or e-mail, and can be personal or predefined. In FIG. 10C, status of communications with a patient can be monitored using various features illustrated in box 49.

Once a change has been made in any of the above areas which utilize a patient's PPM, a case manager may optionally elevate the new dosage prescription to a high priority. In the present invention this may cause delivery of a voice message to the patient that he or she should immediately initiate communications between the patient's PPM and a PAC server in order to receive a revised treatment regimen, including, but not limited to, modified medication doses, modified dosage algorithm(s), and modified fixed and contingent self-monitoring schedules and parameters. If a case manager elects not to elevate the revised monitoring parameters to a high priority level, the altered parameters may be loaded automatically during the next routine data transmission which is prompted by the patient's PPM according to the last transmission.

To make a newly saved prescription (e.g., modified medication doses, modified dosage algorithm(s), and modified fixed and contingent self-monitoring schedules and parameters) available to a patient, a case manager "publishes" the prescription. Publishing a prescription means that an altered prescription, which may be conveyed to a patient via a PPM, is finalized to a point where it is officially ready to be given to the patient. An exemplary user interface 54 for adjusting a patient's physician-prescribed medicine dosage (one of several options) via a patient's PPM is illustrated in FIG. 11. A case manager may see four columns of information representing four quadrants in which adjustments may be enabled. The adjustment parameters may appear in a quadrant in which the insulin dosage being adjusted is assessed. A summary of the insulin dosage, the quadrant in which it is administered, and the average blood glucose measurement it yields appears at the top of the column to help the case manager understand which dosage of insulin is being adjusted. Medications have different time courses of physiologic action. Insulins may differ substantially in this regard. For example, Regular insulin, a short-acting insulin, has a time course such that if taken at breakfast it must be assessed just before lunch. Whereas NPH insulin has a longer time course (an intermediate insulin) and a dosage taken at breakfast is best assessed at dinner.

Figure 12:
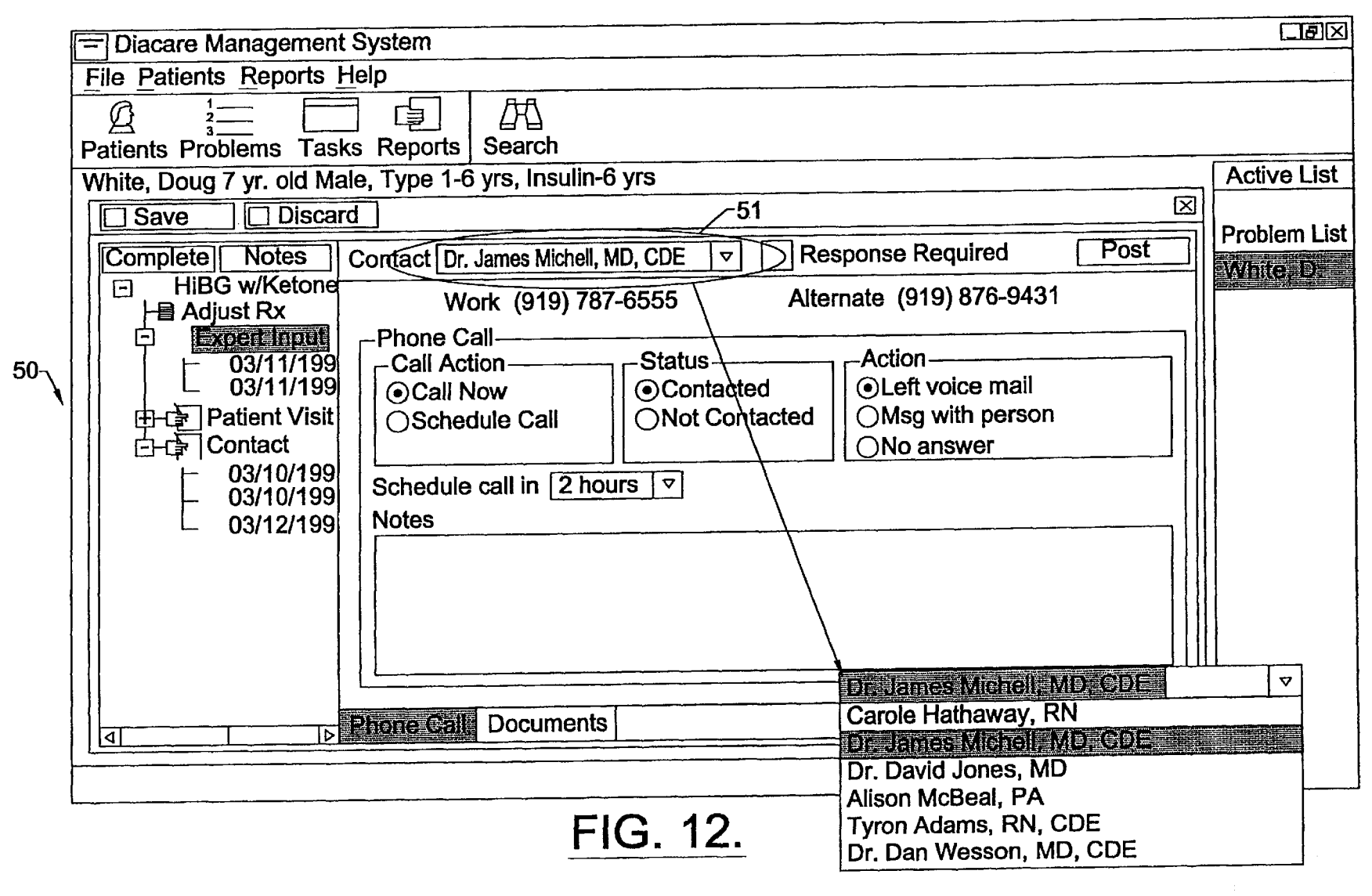

In cases where case managers have questions concerning a patient's medical condition or prescription, case managers may seek input from medical experts using a user interface such as that illustrated in FIG. 12. Expert input may be obtained at any step in the review and alteration process, and may involve referencing current patient data and unresolved medical conditions (if any) with a request for help. Expert input may be directed to a superior (e.g., a supervising case manager or the primary care physician), a specialist (e.g., a diabetologist for questions concerning the primary disease condition) or to a collateral person involved in the patient's care (e.g., a dietitian, optician or podiatrist).

In the illustrated user interface 50 (FIG. 12), expert input may be obtained by selecting a health care giver from the box 51. Preferably, various methods of contacting a selected health care giver are available (e.g., telephone, fax, e-mail, office visit, and the like). Contacts with experts may or may not be accompanied by referenced or attached patient data available from the PAC server. Expert input can be directed to people who may not have direct access to the PAC server and be able to directly review patient data (e.g., a podiatrist), but are more typically directed to others with access to the system and are focused on the patients current medical conditions and overall treatment regimen (endocrinologist or primary care physician). These latter personnel may be expected to provide either advise in written or other form, or may act directly upon (and publish) the overall treatment regimen (medication dosages, dosage adjustment algorithm, or the fixed or contingent self-monitoring schedule) which may be conveyed to the Patient's PPM.

In addition to communicating with patients via a PPM, a case manager may communicate with patients in various ways, such as via telephone, e-mail, AVM and facsimile transmission. Preferably, the present invention provides pre-composed text for inclusion in text-based communications such as letters, faxes and e-mail directed to a patient. Multiple selections can be added to a letter and then edited, or the entire communication can be created manually, and delivery of the text may be done redundantly. Telephone communications may also be managed from a content screen where topic issues can be displayed and optionally highlighted for documentary reasons, and a case manager may elect to immediately make or schedule a patient call, or to schedule voice message delivery of pre-composed or personalized text. Prompting patients to make an overdue transmission of data from his/her PPM to a PAC server may be accomplished using voice message delivery of a pre-composed message. Patient contact options may also be tied to a tickler system to facilitate timely follow-up.

Figure 13:
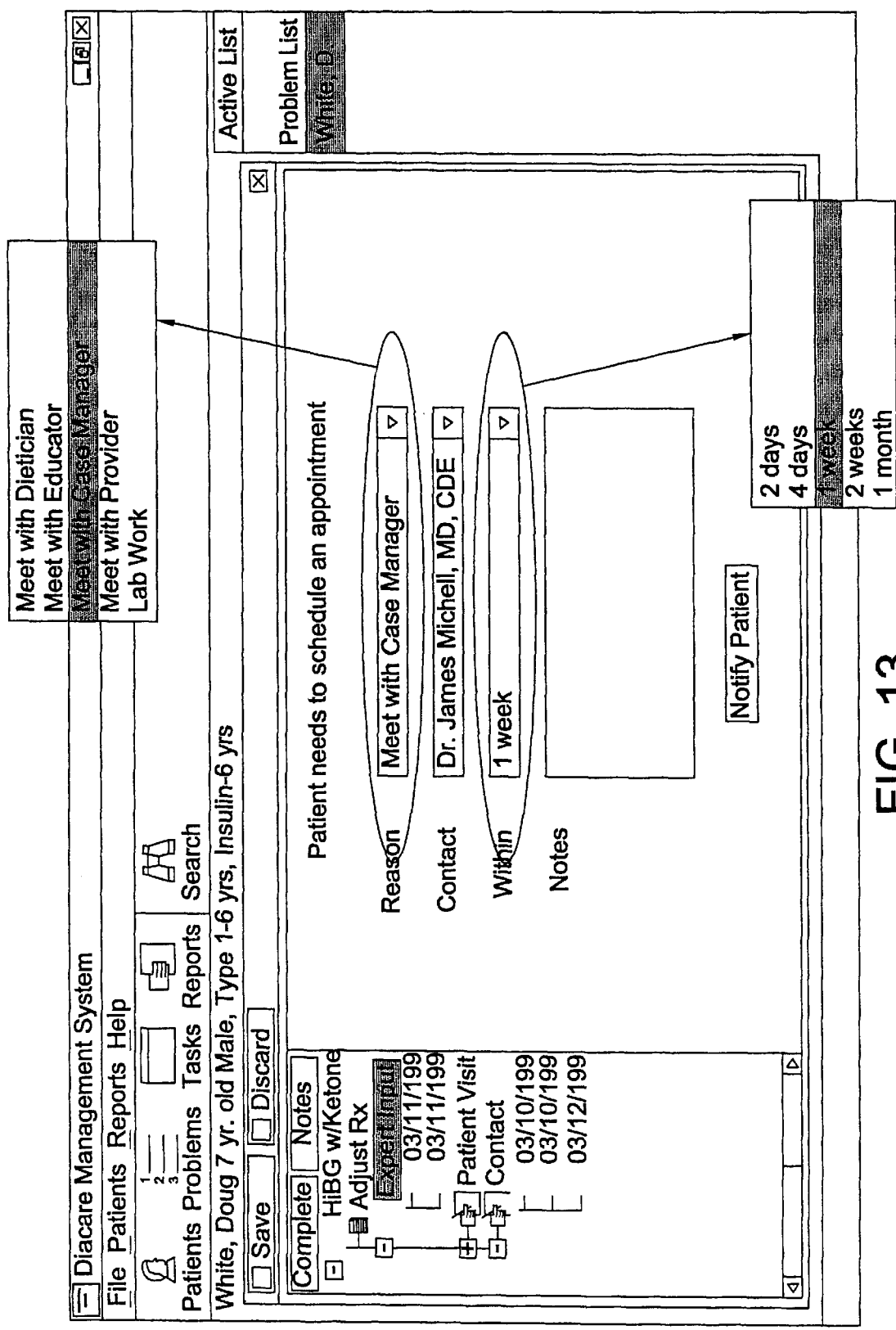
FIG. 13 illustrates an exemplary user interface for facilitating and tracking patient appointments with clinic personnel or other health care providers.

In addition, case managers may utilize the present invention to facilitate and track patient appointments with clinic personnel or other providers involved in health care. An exemplary user interface 56 for this purpose is illustrated in FIG. 13. Once a decision is made to schedule a patient appointment, a system task reminder may be generated that requires periodic follow-up until a record of a scheduled appointment time is input into a PAC server. A case manager may employ a patient's PPM to prompt the patient to make an appointment, and subsequently query the patient for the appointment date once it has been made. Other contact methods may also be employed to prompt a patient to make an appointment and subsequently to inform the case manager concerning the date (e.g., via e-mail, AVM, telephone, and facsimile transmission). A PPM may also be used to verify appointment compliance.

Preferably, the present invention also tracks appointment compliance (e.g., whether a patient kept his/her appointments). Healthcare providers can be sent communications to confirm whenever an appointment has been kept by a patient and to supply associated lab or examination data to a PAC server. To track appointment compliance with providers who cannot directly access a PAC server, a case manager may generate correspondence and associated follow-up reminders in order to obtain confirmation and associated clinical data if desired.

According to another aspect of the present invention, a blind actuarial review of changes made to the medication dosages and/or the rules utilized by a PPM to independently adjust these doses may be utilized. Statistical analysis may optionally be performed on published prescriptions that utilizes pattern analysis, multiple regression, time series and other types of analyses that compare current patient data sets to earlier data and to data of other appropriate patients. This assessment procedure is designed to screen for potential medical conditions whose probability has markedly increased as a result of the most recent prescriptive changes made to a patient's PPM-supported treatment regimen. A secondary purpose involves alerting a case manager in situations where changes made to a prescription are unlikely to result in any significant improvement in a patient's current physiologic condition. In addition, the present invention is also designed to focus a case manager's attention on the areas of a prescription where intervention is likely to result in the greatest improvement in a patient's medical condition.

Figure 14:
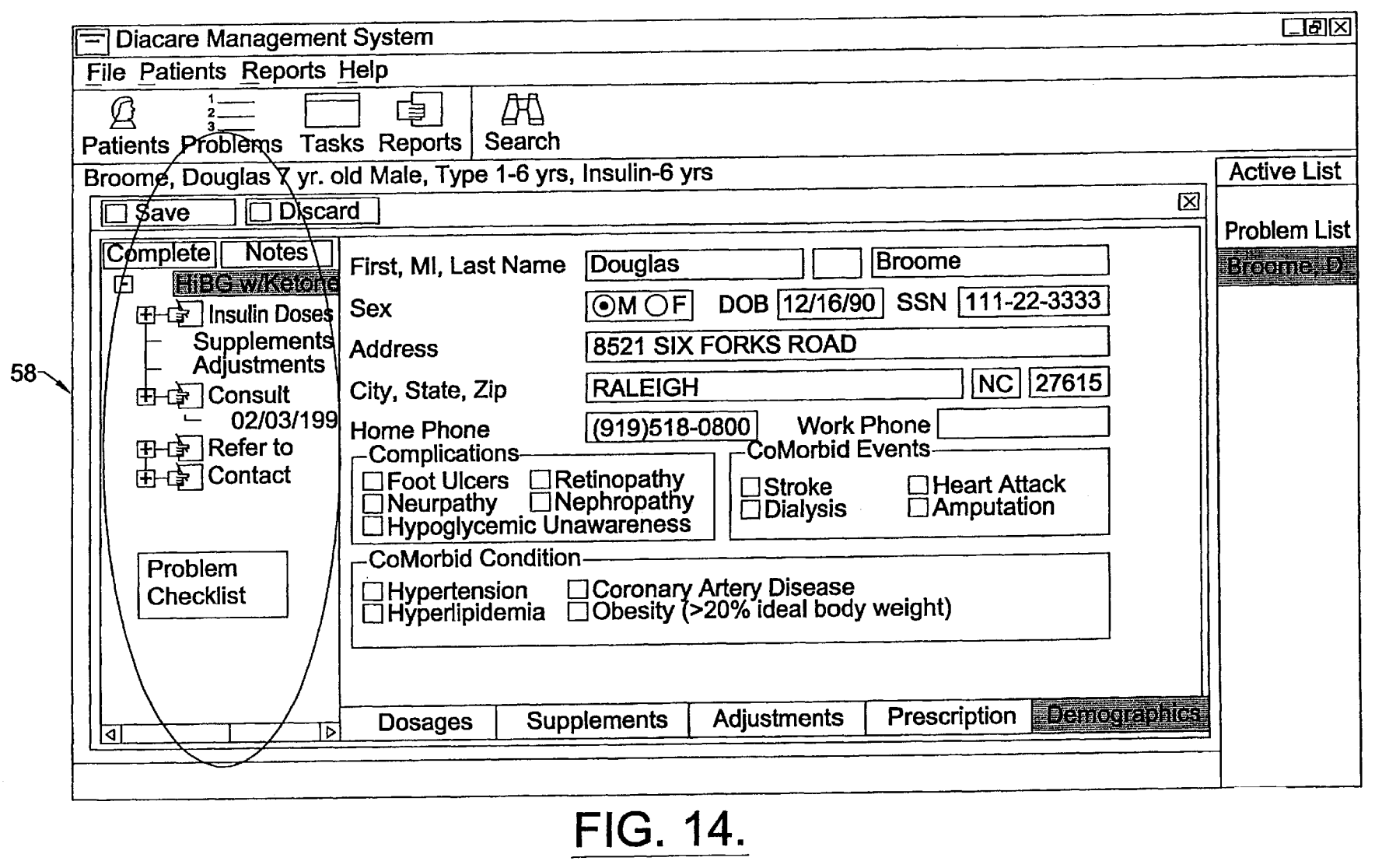

When a medical condition has been corrected, it is effectively removed from a patient's active list by use of a "Complete" button. The user interface 58 of FIG. 14 illustrates a patient's medical condition being removed from the active list. This is graphically illustrated by the addition a check mark in front of the medical condition.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clause are intended to cover the structures described herein as performing the recited function and not only structural equivalents but also equivalent structures.

Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of monitoring, diagnosing and treating medical conditions of a plurality of remotely located patients undergoing anticoagulation therapy, wherein a central data processing system is configured to communicate with and receive data from a plurality of respective patient monitoring systems, wherein each patient monitoring system is capable of receiving and storing patient data, the method-comprising the steps of:

obtaining patient data from a plurality of patient monitoring systems at the central data processing system, wherein the patient data comprises anticoagulation therapy assessment data;

analyzing the obtained patient data from each respective patient monitoring system at the central data processing system to identify medical conditions of each respective patient;

displaying the identified patient medical conditions for each respective patient in selectable, prioritized order according to medical severity; and in response to selecting one of the identified medical conditions for a respective patient, displaying treatment options for treating the medical condition.

2. A method according to claim 1 further comprising the step of communicating treatment information to a respective patient.

3. A method according to claim 2 wherein the step of communicating the treatment information to a respective patient comprises transmitting the treatment information via wireless, satellite, telephone, e-mail, AVM, or facsimile transmission.

4. A method according to claim 2 wherein the step of communicating the treatment information to a respective patient comprises transmitting the treatment information to a respective patient monitoring system.

5. A method according to claim 4 wherein the step of communicating the treatment information to a respective patient monitoring system comprises modifying an anticoagulation medicine dosage algorithm stored within a respective patient monitoring system or within the central data processing system.

6. A method according to claim 1 wherein the step of obtaining patient data from a plurality of patient monitoring systems, further comprises the steps of:

analyzing data transmitted from a patient monitoring system substantially simultaneously with the transmission thereof to the central data processing system to identify emergency medical conditions requiring immediate medical attention; and automatically communicating treatment information to the respective patient monitoring system for an identified emergency medical condition.

7. A method according to claim 1 further comprising the step of determining whether any of the identified medical conditions have been treated.

8. A system for monitoring, diagnosing and treating medical conditions of a plurality of remotely located patients undergoing anticoagulation therapy, comprising:

a plurality of patient monitoring systems, wherein each patient monitoring system is capable of receiving and storing patient data;

a central data processing system configured to communicate with and receive patient data from each of the patient monitoring systems;

means for obtaining patient data from a plurality of patient monitoring systems at said central data processing system, wherein the patient data comprises anticoagulation therapy assessment data;

means for analyzing the obtained patient data from each respective patient monitoring system at said central data processing system to identify medical conditions of each respective patient;

means for displaying the identified patient medical conditions for each respective patient in selectable, prioritized order according to medical severity via at least one remotely located client in communication with said central data processing system; and means for displaying treatment options for treating a displayed medical condition for a respective patient via said at least one remotely located client.

9. A system according to claim 8 further comprising means for communicating the treatment information from said central data processing system to a respective patient.

10. A system according to claim 9 wherein said means for communicating the treatment information from said central data processing system to a respective patient comprises means for transmitting the treatment information via wireless, satellite, telephone, e-mail, AVM or facsimile transmission.

11. A system according to claim 9 wherein said means for communicating the treatment information from said central data processing system to a respective patient comprises means for transmitting the treatment information to a respective patient monitoring system.

12. A system according to claim 11 wherein said means for communicating the treatment information from said central data processing system to a respective patient monitoring system comprises means for modifying an anticoagulation medicine dosage algorithm stored within a respective patient monitoring system or within said central data processing system.

13. A system according to claim 9 wherein said means for communicating the treatment information from said central data processing system to a respective patient comprises means for transmitting treatment information from said at least one client to a respective patient monitoring system.

14. A system according to claim 8 wherein said means for obtaining patient data from a plurality of patient monitoring systems, further comprises:

means for analyzing data transmitted from a patient monitoring system substantially simultaneously with the transmission thereof to the central data processing system to identify emergency medical conditions requiring immediate medical attention; and means for automatically communicating treatment information to the respective patient monitoring system for an identified emergency medical condition.

15. A system according to claim 8 wherein said central data processing system further comprises:

means for monitoring patient usage of medical supplies utilized in anticoagulation therapy; and means for ordering medical supplies for patients that are to be utilized in anticoagulation therapy.

16. A system according to claim 8 wherein said means for displaying the identified patient medical conditions comprises means for displaying selected ones of said identified patient medical conditions.

17. A computer program product for monitoring, diagnosing and treating medical conditions of a plurality of remotely located patients undergoing anticoagulation therapy, wherein a central data processing system is configured to communicate with and receive data from a plurality of respective patient monitoring systems, wherein each patient monitoring system is capable of receiving and storing patient data, said computer program product comprising a computer usable storage medium having computer readable code embodied in said medium, said computer readable code comprising:

computer readable code for obtaining patient data from a plurality of patient monitoring systems at said central data processing system, wherein the patient data comprises anticoagulation therapy assessment data;

computer readable code for analyzing the obtained patient data from each respective patient monitoring system at said central data processing system to identify medical conditions of each respective patient;

computer readable code for displaying identified patient medical conditions for each respective patient in selectable, prioritized order according to medical severity; and computer readable code for displaying treatment options for treating a medical condition responsive to selecting one of the identified medical conditions for a respective patient.

18. A computer program product according to claim 17 further comprising computer readable program code embodied in said medium for communicating the treatment information to a respective patient.

19. A computer program product according to claim 18 wherein said computer readable code for communicating the treatment information to a respective patient comprises computer readable code for transmitting treatment information via wireless, satellite, telephone, e-mail, AVM or facsimile transmission.

20. A computer program product according to claim 18 wherein said computer readable program code for communicating the treatment information to a respective patient comprises computer readable program code for transmitting treatment information to a respective patient monitoring system.

21. A computer program product according to claim 20 wherein said computer readable program code for communicating the treatment information to a respective patient monitoring system comprises computer readable program code for modifying an anticoagulation medicine dosage algorithm stored within a respective patient monitoring system.

22. A computer program product according to claim 17 wherein said computer readable program code for obtaining patient data from a plurality of patient monitoring systems, further comprises:

computer readable program code for analyzing data transmitted from a patient monitoring system substantially simultaneously with the transmission thereof to the central data processing system to identify emergency medical conditions requiring immediate medical attention; and computer readable program code for automatically communicating treatment information to the respective patient monitoring system for an identified emergency medical condition.

23. A computer program product according to claim 17 further comprising computer readable program code for determining whether any of the identified medical conditions have been treated.

24. A computer program product according to claim 17 further comprising:
   computer readable program code means for monitoring patient usage of medical supplies utilized in anticoagulation therapy; and
   computer readable program code means for ordering medical supplies for patients that are to be utilized in coagulation therapy.

25. A portable apparatus for monitoring, diagnosing and treating medical conditions of a patient undergoing anticoagulation therapy, comprising:
   means for receiving and storing patient data provided by a patient, wherein the patient data includes at least one of physiological data, biological data and behavioral data;
   at least one anticoagulation medicine dosage algorithm stored within the portable apparatus for using the stored patient data to generate medicine dosage recommendations in real time;
   means for communicating with and transmitting the stored patient data to a remotely located data processing system; and
   means for receiving treatment information from said remotely located data processing system.

26. A portable apparatus according to claim 25 further comprising:
   a database of medication interaction information; and
   means for allowing the patient to query the database for information related to patient usage of multiple medications.

27. A portable apparatus according to claim 25 wherein said means for receiving treatment information from said remotely located data processing system comprises means for modifying said at least one anticoagulation medicine dosage algorithm stored within said portable apparatus.

28. A portable apparatus according to claim 25 further comprising means for displaying treatment information received from said remotely located data processing system to the patient.

29. A system for monitoring, diagnosing and treating medical conditions of a plurality of remotely located patients undergoing anticoagulation therapy, comprising:
   a central data processing system configured to communicate with a plurality of remotely located patient monitoring systems;
   means for obtaining patient data from each of said plurality of remotely located patient monitoring systems, wherein the data comprises prothrombin time (PT) data;
   means for analyzing the obtained patient data from each respective patient monitoring system at said central data processing system to identify medical conditions of each respective patient;
   at least one remotely located client in communication with said central data processing system; and
   means for displaying the identified patient medical conditions for each respective patient in selectable, prioritized order according to medical severity via said at least one remotely located client.

30. A system according to claim 29 further comprising means for displaying treatment options for treating a selected medical condition for a respective patient via said at least one remotely located client.

31. A system according to claim 29 further comprising means for analyzing the obtained patient data from a patient monitoring system using a warfarin dosage algorithm to determine if a change in medication dosage is necessary.

32. A system according to claim 31 further comprising means for communicating changes in warfarin dosage to a patient.

33. A system according to claim 29 further comprising means for communicating treatment information from said central data processing system to a respective patient.

34. A system according to claim 33 wherein said means for communicating the treatment information from said central data processing system to the respective patient comprises means for transmitting the treatment information via wireless, satellite, telephone, e-mail, AVM or facsimile transmission.

35. A system according to claim 34 wherein said means for communicating the treatment information from said central data processing system to the respective patient monitoring system comprises means for modifying a warfarin dosage algorithm stored within a respective patient monitoring system.

36. A system according to claim 33 wherein said means for communicating the treatment information from said central data processing system to the respective patient comprises means for transmitting the treatment information to a respective patient monitoring system.

37. A system according to claim 33 wherein said means for communicating treatment information from said central data processing system to a respective patient comprises means for transmitting the treatment information from said at least one client to a respective patient monitoring system.

38. A system according to claim 29 wherein said means for obtaining patient data from a plurality of patient monitoring systems, further comprises:
   means for analyzing data transmitted from a patient monitoring system substantially simultaneously with the transmission thereof to the central data processing system to identify emergency medical conditions requiring immediate medical attention; and
   means for automatically communicating treatment information to the respective patient monitoring system for an identified emergency medical condition.

39. A system according to claim 29 wherein said central data processing system further comprises:
   means for monitoring patient usage of medical supplies utilized in anticoagulation therapy; and
   means for ordering medical supplies for patients that are to be utilized in anticoagulation therapy.

40. A method of monitoring, diagnosing and treating medical conditions of a plurality of remotely located patients undergoing anticoagulation therapy, wherein a central data processing system is configured to communicate with and receive data from a plurality of respective anticoagulation therapy monitoring devices, wherein each respective anticoagulation therapy monitoring device is capable of receiving and storing patient data, the method comprising the steps of:
   obtaining patient data from a plurality of anticoagulation therapy monitoring devices at the central data processing system, wherein the patient data comprises prothrombin (PT) data;
   analyzing the obtained patient data from each respective anticoagulation therapy monitoring device at the central data processing system to identify medical conditions of each respective patient;

displaying the identified patient medical conditions for each respective patient in selectable, prioritized order according to medical severity; and in response to selecting one of the identified medical condition for a respective patient, displaying treatment options for treating the medical condition.

41. A method according to claim 40 further comprising the step of communicating treatment information to a respective patient.

42. A method according to claim 41 wherein said step of communicating the treatment information to a respective patient comprises transmitting the treatment information via wireless, satellite, telephone, e-mail, AVM or facsimile transmission.

43. A method according to claim 41 wherein said step of communicating the treatment information to a respective patient comprises transmitting treatment information to a respective anticoagulation therapy monitoring device.

44. A method according to claim 43 wherein said step of communicating treatment information to a respective anticoagulation therapy monitoring device comprises modifying a warfarin dosage algorithm stored within a respective anticoagulation therapy monitoring device.

45. A method according to claim 40 wherein the step of obtaining patient data from a plurality of anticoagulation therapy monitoring devices, further comprises the steps of:

analyzing data transmitted from an anticoagulation therapy monitoring device substantially simultaneously with the transmission thereof to the central data processing system to identify emergency medical conditions requiring immediate medical attention; and automatically communicating treatment information to the respective anticoagulation therapy monitoring device for an identified emergency medical condition.

46. A method according to claim 40 further comprising the step of determining whether any of the identified medical conditions have been treated.

47. A portable apparatus for monitoring, diagnosing and treating medical conditions of a patient undergoing anticoagulation therapy, comprising:

means for receiving and storing patient blood data and behavioral data;

a warfarin dosage algorithm stored within the apparatus for using the stored patient blood data and behavioral data to generate warfarin dosage recommendations in real time;

means for communicating with and transmitting the stored patient blood data and behavioral data to a remotely located data processing system; and means for receiving treatment information from said remotely located data processing system.

48. A portable apparatus according to claim 47 further comprising:

a database of medication interaction information; and means for allowing the patient to query the database for information related to patient usage of multiple medications.

49. A portable apparatus according to claim 47 wherein said means for receiving treatment information from said remotely located data processing system comprises means for modifying said warfarin dosage algorithm stored within said portable apparatus.

50. A portable apparatus according to claim 47 further comprising means for displaying the treatment information received from said remotely located data processing system to the patient.

51. A system for monitoring, diagnosing and treating medical conditions of a plurality of remotely located patients undergoing anticoagulation therapy, comprising:

a central data processing system configured to communicate with a plurality of remotely located anticoagulation therapy monitoring devices;

means for obtaining patient data from each of said plurality of remotely located anticoagulation therapy monitoring devices, wherein the patient data comprises prothrombin (PT) data;

means for analyzing the obtained patient data from each respective anticoagulation therapy monitoring device at said central data processing system to identify medical conditions of each respective patient;

at least one remotely located client in communication with said central data processing system; and means for displaying the identified patient medical conditions for each respective patient in selectable, prioritized order according to medical severity via said at least one remotely located client.

52. A system according to claim 51 further comprising means for displaying treatment options for treating a selected medical condition for a respective patient via said at least one remotely located client.

53. A system according to claim 51 further comprising means for communicating the treatment information from said central data processing system to a respective patient.

54. A system according to claim 53 wherein said means for communicating the treatment information from said central data processing system to the respective patient comprises means for transmitting the treatment information via wireless, satellite, telephone, e-mail, AVM or facsimile transmission.

55. A system according to claim 53 wherein said means for communicating the treatment information from said central data processing system to the respective patient comprises means for transmitting the treatment information to a respective anticoagulation therapy monitoring device.

56. A system according to claim 55 wherein said means for communicating the treatment information from said central data processing system to the respective patient monitoring system comprises means for modifying a warfarin dosage algorithm stored within a respective anticoagulation therapy monitoring device.

57. A system according to claim 53 wherein said means for communicating the treatment information from said central data processing system to the respective patient comprises means for transmitting the treatment information from said at least one client to a respective anticoagulation therapy monitoring device.

58. A system according to claim 51 wherein said means for obtaining patient data from a plurality of anticoagulation therapy monitoring devices, further comprises:

means for analyzing data transmitted from a anticoagulation therapy monitoring device substantially simultaneously with the transmission thereof to the central data processing system to identify emergency medical conditions requiring immediate medical attention; and means for automatically communicating treatment information to the respective anticoagulation therapy monitoring device for an identified emergency medical condition.

59. A system according to claim 51 wherein said central data processing system further comprises:

means for monitoring patient usage of medical supplies utilized in anticoagulation therapy; and means for ordering medical supplies to be utilized in anticoagulation therapy.

* * * * *